United States Patent
Karube et al.

(10) Patent No.: US 6,537,800 B1
(45) Date of Patent: Mar. 25, 2003

(54) APPARATUS FOR AUTOMATICALLY MEASURING MINUTE MEMBRANE POTENTIAL

(75) Inventors: Isao Karube, Kanagawa (JP); Takashi Saitoh, Tokyo (JP)

(73) Assignee: Center for Advanced Science and Technology Incubation, Ltd., Tokyo (JP)

( * ) Notice: Subject to any disclaimer, the term of this patent is extended or adjusted under 35 U.S.C. 154(b) by 0 days.

(21) Appl. No.: 09/623,969
(22) PCT Filed: Mar. 12, 1999
(86) PCT No.: PCT/JP99/01224
§ 371 (c)(1),
(2), (4) Date: Dec. 28, 2000
(87) PCT Pub. No.: WO99/46588
PCT Pub. Date: Sep. 16, 1999

(30) Foreign Application Priority Data

Mar. 12, 1998 (JP) ............................................. 10/080182

(51) Int. Cl.[7] .............................................. C12M 1/34
(52) U.S. Cl. ............................... 435/287.1; 435/285.2; 204/403.13
(58) Field of Search ......................... 435/285.2, 287.1; 204/403.13, 403.01, 290.01

(56) References Cited

PUBLICATIONS

Saito et al. 'Light does and time dependency of photodynamic cell membrane damage.' Photochemistry and Photobiology. vol. 68 (1998) No. 5, pp. 745–748.*
Robinson, D. A., "The Electrical Properties of Metal Microelectrodes," *Proceedings of the IEEE*, 56:1065–1071 (1968).

Hamill, O. P., et al., "Improved Patch–Clamp Techniques for High–Resolution Current Recording from Cells and Cell–Free Membrane Patches," *Pflügers Archiv*, 391:85–100 (1981).
Kurata S., et al., "The Laser Method for Efficient Introduction of Foreign DNA into Cultured Cells," *Experimental Cell Research*, 162:372–378 (1986).
Valenzeno, D. P., "Photomodification of Biological Membranes with Emphasis on Singlet Oxygen Mechanisms," *Photochemistry and Photobiology*, 46:147–160 (1987).
Horn, R., et al., "Muscarinic Activation of Ionic Currents Measured by a New Whole–Cell Recording Method," *J. Gen. Physiol.*, 92:145–159 (1988).
Levitan, E. S., et al., "Neuropeptide Modulation of Single Calcium and Potassium Channels Detected with a New Patch Clamp Configuration," *Nature*, 348:545–547 (1990).
Bard, A. J., et al., "Chemical Imaging of Surfaces with the Scanning Electrochemical Microscope," *Science*, 254:68–74 (1991).

(List continued on next page.)

Primary Examiner—William H. Beisner
(74) Attorney, Agent, or Firm—Nixon Peabody LLP

(57) ABSTRACT

An apparatus for automatically measuring minute membrane potential, based on a technique developed for controlling a membrane denaturation reaction without using a physical shearing force, for example, a method of causing the destruction of membrane at a limited portion of a living membrane by making a stimulus, such as light and a compound activated by the stimulus react with each other in a membrane, such as a living membrane, this method being applied to a minute electrode to facilitate the insertion thereof into a cell, which has been difficult in the use of a minute metal electrode, and enable membrane potential in a cell to be measured easily, the minute metal electrode enabling the integration thereof and the development of a neural interface in the barrier-free technology.

13 Claims, 16 Drawing Sheets

OTHER PUBLICATIONS

Marles, R. J., et al., "Thiophenes as Mosquito Larvicides: Structure–Toxicity Relationship Analysis," *Pesticide Biochemistry And Physiology*, 41:89–100 (1991).

Altin, J. G., et al., "Testing the In Vivo Role of Protein Kinase C and c–Fos in Neurite Outgrowth by Microinjection of Antibodies into PC12 Cells," *Molecular Biology of the Cell*, 3:323–333 (1992).

Jimbo, Y., et al., "Electrical Stimulation and Recording from Cultured Neurons Using a Planar Electrode Array," *Bioelectrochemistry and Bioenergetics*, 29:193–204 (1992).

Kovacs, G. T. A., et al., "Regeneration Microelectrode Array for Peripheral Nerve Recording and Stimulation," *IEEE Transaction on Biomedical Engineering*, 39:893–902 (1992).

Hoogerwerf, A. C., et al., "A Three–Dimensional Microelectrode Array for Chronic Neural Recording," *IEEE Transactions on Biomedical Engineering*, 41:1136–1146 (1994).

Thorpe, W. P., et al., "Dynamics of Photoinduced Cell Plasma Membrane Injury," *Biophysical Journal*, 68:2198–2206 (1995).

Boch, R., et al., "Study of Photoinduced Energy and Electron Transfer in α–Terthienyl–Bovine Serum Albumin Conjugates: A Laser Flash Photolysis Study," *Photochemistry and Photobiology*, 64:92–99 (1996).

Haydon, P. G., et al., "Membrane Deformation of Living Glial Cells Using Atomic Force Microscopy," *Journal of Microscopy*, 182:114–120 (1996).

Jacobs, H. O., et al., "Surface Potential Mapping: A Qualitative Material Contrast in SPM," *Ultramicroscopy*, 69:39–49 (1997).

Henriksen G. H., et al., "Laser–Assisted Patch Clamping: A Methodology," *Pflügers Archiv*, 433:832–841 (1997).

* cited by examiner

1. MEMBRANE STRUCTURE
2. SUPPORT
3. MEMBRANE DENATURATION PROMOTING PORTION
4. DENATURED PORTION OF MEMBRANE

1. MEMBRANE STRUCTURE
2. SUPPORT
3. MEMBRANE DENATURATION PROMOTING PORTION
4. DENATURED PORTION OF MEMBRANE

1. MEMBRANE STRUCTURE
2. SUPPORT
3. MEMBRANE DENATURATION PROMOTING PORTION
4. DENATURED PORTION OF MEMBRANE

1. MEMBRANE STRUCTURE
2. SUPPORT
3. LIQUID CONTAINING MEMBRANE DENATURATION PROMOTER
4. DENATURED PORTION OF MEMBRANE

1. MEMBRANE STRUCTURE
2. SUPPORT
3. MEMBRANE DENATURATION PROMOTING PORTION
4. DENATURED PORTION OF MEMBRANE

1.) EXECUTE NORMAL MICROINJECTION TO CHECK WHETHER Z LIMIT HAS BEEN APPROPRIATELY SET.

2.) CHANGE SETTINGS SUCH THAT APPROACH IS MADE AT SPEED AT WHICH INSERTION IS DIFFICULT, AND EVALUATE EFFECTS OF PHOTOSENSITIZING ON INJECTION EFFICIENCY.

BAT-LY-LIGHT: LY+BAT CONTAINING LIQUID; PHOTOSENSITIZING INJECTION; ATTEMPTED ON 32 CELLS
BAT-LY: LY+BAT CONTAINING LIQUID; NORMAL INJECTION; ATTEMPTED ON 30 CELLS
LY: LY CONTAINING LIQUID; NORMAL INJECTION; ATTEMPTED ON 29 CELLS

APPARATUS FOR AUTOMATICALLY MEASURING MINUTE MEMBRANE POTENTIAL

TECHNICAL FIELD

The present invention relates to an apparatus for measuring minute membrane potential, which measures a difference in potential between areas separated by a membrane or different positions on a membrane, such as an interior and exterior of a cell membrane, as well as an electrode constituting this apparatus.

BACKGROUND ART

To deal with an aging society, a technical research area for directly supporting human lives is being expanded. This is called a "barrier-free technology" which supports deteriorated or lost functions of human bodies by improving the physical structures of social infrastructures such as towns and houses or developing new personally available equipment. Technical developments based on this concept contribute to creating an environment where human beings live easy social lives whether or not they are physically handicapped.

The barrier-free technology initially concentrated on electronics, machinery, and construction but is being gradually expanded; some recent studies for the barrier-free technology are directly related to medicine. Typical examples include research on advanced medical equipment such as functional artificial hands or legs which supplement the functions of the bodies of handicapped people or the like. Such equipment is now controlled using methods such as electromyographic detection or detection of motions of the eyes or tongue, but information obtained by these input means is quantitatively significantly insufficient in terms of the amount of information required for motor and sensory functions of living bodies. If, for example, a person has lost his hand or leg due to a traffic accident, or a war wound, he must have an artificial hand or leg. However, to control the operation of the artificial hand or leg as if it were an actual hand or leg and to feed back senses for temperature or contacts to the human body, a certain interface is required which can simultaneously measure action potential generated by individual nerves of a bundle of several hundred peripheral nerves and then input a corresponding signal. Already developed such interfaces, however, are all insufficient.

One of the most successful examples in the field of direct exchange of information between nerves and electronic equipment is equipment called artificial inner ear [Rehabilitation Medicine, 31, 233–239 (1994)]. If an auditory defect occurs such that a portion between the tympanic membrane and the inner ear is prevented from functioning, the artificial inner ear executes the function of this portion by directly stimulating auditory nerves in the cochlear organ. The artificial inner ear processes a sound input through a microphone depending on the auditory characteristic of this person to generate a digital signal in order to electrically stimulate terminals of the auditory nerves, that is, cochlear nerves. Spherical electrodes are generally arranged at about 22 locations inside the cochlea, where about 30,000 auditory nerves are located, to input a sound signal to the nerves through the electrodes. For some time after the artificial inner ear has been implanted, most subjects feel that they hear very strange sounds, but once information processing in the brain has been adapted to the artificial inner ear, the subjects can distinguish sounds. Analysis and improvements of electrodes for the artificial inner ear is a large research area.

A substantial reduction in input auditory information from an inherent input through 30,000 nerves to an artificial input through about 22 electrodes means that auditory information received by the brain also decreases down to 0.1% or less. Thus, regeneration of the sound listening ability depends on whether the brain can supplement and understand a substantially reduced amount of information. Several months are required to optimally adapt the auditory processing function of the brain to the artificial inner ear. The artificial inner ear suggests possibilities of nerve interfaces.

With the artificial inner ear, however, the electrodes are installed in the cochlear organ, where nerve terminals are exposed and lie over several centimeters. The nerve stimulating electrodes may be installed at nerve terminals exposed to the interior of the organ, so that it is not physically difficult to arrange the electrodes. In addition, in inputting a sound signal, it is very easy to analyze and determine those of the nerves which receive the signal and the frequency of the signal that can be received by these nerves. In this manner, the reasons why the artificial inner ear has successfully been put to practical use include many appropriate conditions for transmission of signals to the nerves through the electrodes. In other words, it is virtually impossible to directly apply the electrode technology for the artificial inner ear to nerves other than the cochlear nerves.

Many research institutes in the world are developing interfaces for exchanging information between nerve cells and electronic equipment; these studies can be roughly classified into two aspects.

One of them is a medical technological approach where minute electrodes are implanted in a nerve bundle or the brain [IEEE Trans. Biomed. Eng., 39, 893–902 (1992)] [IEEE Trans. Biomed. Eng. 41, 567–577 (1994)] [IEEE Trans. Biomed. Eng., 41, 305–313 (1994)]. This approach attempts to provide terminals for obtaining a control signal for rehabilitation equipment directly from nerves or multi-channel connection terminals for inputting a signal to nerves.

The other aspect is based on a long-term prospect for application of the information processing ability of nerve cells to computers [Bioelectrochemistry and Bioenergetics, 29, 193–204 (1992)] [Brain Research, 446, 189–194 (1988)]. This approach pursues the possibilities of what is called "biocomputers" that use living cells as operation elements.

Conventional nerve interfaces are roughly classified into the following three types:
(a) Aggregate needle-shaped metal electrodes and needle point holder-shaped aggregate metal needle electrodes [IEEE Trans. Biomed. Eng., 41, 1136–1146 (1994)]
(b) Axon regenerated matrix electrodes [IEEE Trans. Biomed. Eng., 39, 893–902 (1992)] [IEEE Trans. Biomed. Eng., 41, 567–577 (1994)] [IEEE Trans. Biomed. End., 41, 305–313 (1994)]
Flat cultured-nerve-cell electrodes on a substrate [Bioelectrochemistry and Bioenergetics, 29, 193–204 (1992)] [Brain Research, 446, 189–194 (1992)]

Needle-shaped electrodes for measuring nerves have been used since the initial period of research on nerves, but the study of microneurography was the first to record the action potential of a single human peripheral nerve in situ [Clinical Electroencephalogram, 25, 493–500, 564–571, 629–638 (1983)]. The needle point holder-shaped electrode is one of the aggregate types in which this electrode is formed at a tip of a needle or on a side thereof and which is struck to a severed nerve bundle or a tissue in the brain [IEEE Trans. Biomed. Eng., 41, 1136–1146 (1994)]. That is, the needle point holder-shaped electrode is obtained by three-dimensionally expanding the needle-shaped electrode using a micromachine technology. In a basic design, the needle-shaped electrode records a faint extracellular current from a nerve that is accidentally located close to the electrode section. Although the needle-shaped electrode can be used to measure a single nerve cell, this method is evidently not accurate enough to simultaneously measure a large number of nerves even if the degree of integration of needle-shaped electrodes is increased to enhance spatial resolution, because the relative distance between each nerve and the electrode depends on accidents.

The axon regenerated matrix electrode in 2 is a field that has been expanded since 1992 when Stanford University conducted a relevant study, and many reports have recently been made on this electrode [IEEE Trans. Biomed. Eng. 39, 893–902 (1992)] [IEEE Trans. Biomed. Eng., 41, 567–577 (1994)] [IEEE Trans. Biomed. ENg., 41 305–313 (1994)]. This electrode is obtained by integrating electrodes into a 16×16 matrix or the like with a hole formed in each electrode section. The electrode is sandwiched between severed portions of a nerve bundle to record an extracellular current from each nerve axon regenerated through the corresponding hole in the electrode. The axon regenerated electrode is advantageous in that the axon and the electrode are physically stably joined together and that a signal from the nerve axon passed through the hole in the electrode can be identified and detected. However, severing the nerve bundle obviously adversely affects the nerves, and the nerve axons regenerated through the holes in the electrodes amounts to only several percents of the entire nerve bundle. The axon regenerated electrode is expected to have its degree of integration increased so as to detect current in each nerve to electrically stimulate each nerve. If, however, attempts are made to increase the degree of integration, the area of the electrode section per nerve must be reduced while the area required for a wiring section of the electrode must be increased. Consequently, the rate of opening necessarily declines to significantly affect the spatial resolution.

The flat electrode method in 3 is often used for basic studies for biocomputers [Bioelectrochemistry and Bioenergetics, 29, 193–204 (1992)] [Brain Research, 446, 189–194 (1988)]. In terms of extension of axons of nerve cells, various useful information has been obtained on the shape and material of a substrate to which a cell or an axon adheres and on an applied voltage. A problem of this method, however, is a small contact area between the electrode and the cell. A sufficient voltage and a sufficient contact area between the electrode and the cell are required to generate an action potential from the cell. Application of a high voltage, however, results in electrolysis of moisture, which is essential for a cell environment when the voltage exceeds about 1.3 V. Thus, the applicable voltage is limited. Since current density is also limited, the contact area between the cell and the electrode must necessarily be increased in order to effectively stimulate the cell. As a result, it is impossible to stimulate each single nerve cell, and the only possible method is to stimulate a mass of nerve cells on the electrode to obtain an integration effect.

A common disadvantage of these existing nerve interference is that they use the extracellular electrode to measure an electromotive force of about several $\mu v$ induced by an action potential in the nerve based on a minor change in the concentration of ions outside the cell membrane. First, when the spatial resolution of the electrode is increased, the electrode picks up extracellular currents from cells in the neighborhood. Second, when the nerve is electrically stimulated to input a signal thereto, the electrode must provide a current much higher than an extracellular current from the nerve, thereby preventing measurements by other electrodes in the neighborhood.

The essence of nerve information is a membrane potential pulse from the nerve cell having a variation of about 100 mV. Accordingly, appropriate electrodes for use in exchanging information between the nerve and the equipment must be able to contact hard with the cell membrane or to be inserted through the cell membrane in order to measure variations in membrane potential.

The above-described interfaces using the extracellular electrodes can obtain a certain amount of information from the nerve and stimulate the nerve. None of these electrodes, however, has an enough spatial resolution to join to each nerve axon on a one-to-one correspondence, the nerve axon constituting a fiber for transmitting information. This is essentially disadvantageous in mutually separating nerve signals. Except for the central and terminal portions, the entire nerve axon has a mixture of inputs from a sensory organ to the center (afferent nerve fibers) and outputs from the center to a muscle or the like (efferent nerve fibers). Thus, when these interfaces have a low spatial resolution, input signals from the sensory organ and output signals to the muscle or the like are likely to be crossed. When nerve signals obtained are resolved and separated into signals for the individual nerves, a problem occurs even with the matrix electrode, which appears to have been most successful among the interfaces and which have been experimented in the situ systems.

That is, in controlling such human body supporting equipment, the biggest problem to be solved is how to efficiently exchange information directly between a normal nerve system and the electronic equipment. Thus, various research institutes are studying "nerve interfaces" using electrodes that can each be connected directly to a nerve, which is a source of living information, in order to transmit information between the nerve and various equipment.

As described above, almost all the disadvantages of the existing nerve interfaces are related to the use of the extra-cellular electrodes. The current electrodes that can input and output information to and from the individual nerve cell through the cell membrane include minute electrodes and patch lamp electrodes both used for electrophysicological experiments. The problems listed below, however, must be solved before these methods can be used for actual applications.

1) Although a tip portion of the electrode which contacts with the cell is thin and has a diameter between 200 nm and 2 $\mu$m, it is essential to integrate these electrodes together because their main body is composed of a glass tube of diameter several millimeters.

2) When the electrode is connected to the cell, it may destroy the cell membrane unless vibration of a measuring system is minimized.

3) Since an operation of connecting the electrodes to the cell is difficult, skills are required for the connection operation.

To insert an existing electrode into the cell, a physical shearing force must be applied to the electrode to destroy the cell membrane. If the electrode uses as a support, a material of a high physical strength such as glass, the cell membrane can be destroyed by applying a physical shearing force to the electrode. This method, however, is inappropriate for minute metal electrodes in terms of structure and strength.

The existing cell membrane destroying method using only a physical shearing force is not the best method because the membrane is shaped for a high fluidity. That is, a sharp electrode alone cannot always penetrate the cell membrane. It is particularly difficult to insert the electrode into a cell in the order of several tens of micrometers simply by physically pressing the electrode into the cell. A major reason why the patch electrode [Nature, 260, 799–802 (1976)][Pflugers Arch., 391, 85–100 (1981)] has been designed is that even the minute glass electrode, which is relatively strong, has the above problem; it is thus important to improve the electrode inserting method.

Some reports on the measurement of surfaces of living nerve cells using atomic force microscope show that the cells were not damaged to the degree that the cytoplasm was subjected to leakage despite an increase in a contact pressure of a probe for scanning and measuring a surface shape [Journal of Microscopy (Oxford), 182, 114–120 (1996)]. This is because the cell membrane is composed of phospholipid, which has a high fluidity. This high fluidity was clarified through studies of cell fusion at the end of the 1970s [Proc. Natl. Acad. Sci. 69, 2056–2060 (1972)][J. Am.Chem.Soc., 94, 4475–4481 (1972)][Biochem.Med., 15, 212–216 (1976)].

It is thus contemplated that temporary and partial destruction of the cell membrane is used to assist the insertion of the electrode. Such a cell membrane destroying method requires a destroyed portion and the amount of destruction to be controlled. Enzymatic destruction using lipase or protease or a method using β-rays or laser beams are possible, but the inventors have focused on a phospholipid radical chain peroxidation reaction as an example of destruction of the cell membrane using a method other than the physical shearing force.

Activated oxygen such as singlet oxygen or superoxide radicals peroxidizes unsaturated phospholipid in the cell membrane through a chain reaction. In contrast, the cell has an oxidation defending mechanism such as α-tocopherol (vitamin E), which is an agent for capturing radicals in the membrane), or L-ascorbic acid (vitamin C) or superoxide dismutase (SOD), which is a water-soluble antioxidant, to resist oxidation. Defects in cells originating from radicals and the detailed mechanism of oxidation and defense there against are described in the document ["Free Radicals in Biology and Medicine", Oxford University Press (1985)].

When such a chain oxidation action exceeds the oxidation defending capability, the destruction of the phospholipid membrane progresses rapidly and exponentially to deprive an ion penetration inhibiting capability of the cell membrane, thereby disabling the cell from maintaining metabolism.

Molecules that generate activated oxygen to trigger this lipid chain peroxidation reaction when irradiated with light are called "photosensitizers (PS)". General photosensitizers include rose bengal and porphyrin.

By using such a photosensitizer to modify the electrode so that it can act as a membrane destroyer to allow the electrode to penetrate the cell membrane, the cain peroxidization reaction has only to be effected on a minimum area of a target cell surface for a short period of time. Moreover, if the membrane is damaged due to the peroxidation reaction during an electrode inserting operation, it is expected to be repaired by the above-described antioxidation system after the insertion.

DISCLOSURE OF THE INVENTION

It is a basic object of the present invention to develop a technology for controlling the destruction of the cell membrane. For applications the simply require the cell to be destroyed, various poisons have been examined for a long time. No technology has met the cell technology's need to partially and temporarily destroy the cell membrane without causing cell death. In addition, the physical-shearing-force-based method using minute glass tubes or the like is limited. That is, it is an object of the present invention to develop a technology for using a method other than the physical shearing force to punch a living membrane while controlling the destruction of the membrane, that is, a membrane destruction controlling technology, thereby developing an electrode that can denature or destroy the membrane and that can be put to practical use.

To punch the living membrane while controlling the destruction thereof, a destroyed portion and the amount of destruction must be controlled. Thus, the inventors have developed a method for enabling the membrane to be denatured or punched while controlling activation of membrane destruction.

Although it is possible to temporarily and partially denature/destroy the membrane using enzymatic destruction with lipase or protease or using β-rays or laser beams, the inventors have focused on a phospholipid radical chain peroxidization reaction as an example of destruction of the cell membrane using a method other than the physical shearing force.

Activated oxygen such as singlet oxygen or superoxide radicals peroxidizes unsaturated phospholipid in the cell membrane through a chain reaction. In contrast, the cell has an oxidation defending mechanism such as β-tocopherol (vitamin E), which is an agent for capturing radicals in the membrane), or L-ascorbic acid (vitamin C) or superoxide dismutase (SOD), which is a water-soluble antioxidant, to resist oxidation.

When such a chain oxidation action exceeds the oxidation defensing capability, the destruction of the phospholipid membrane progresses rapidly and exponentially to deprive an ion penetration inhibiting capability of the cell membrane, thereby disabling the cell from maintaining metabolism. As this chain membrane destruction progresses, the cell is finally killed.

Molecules that generate activated oxygen a trigger this lipid chain peroxidization reaction when irradiated with light are called "photosensitizers (PS)". General photosensitizers include rose bengal and porphyrin.

By using such a photosensitizer as a membrane denaturant, the chain peroxidization reaction has only to be effected partly on a target cell surface, that is, in a minimum area thereof for a short period of time, in order to denature the membrane. Moreover, if the membrane is damaged due to the peroxidization reaction during an electrode punching operation, it is expected to be repaired due to the fluidity of the membrane itself or by the above-described antioxidation system after the punching.

The inventors applied 5'5"-bis(aminomethyl)-2,2,':5'2"-terthiophene dihydrochloride (BAT), one of the photosensitizers, to surface membranes of cultured cells PC12 from the nerve system. The photosensitizer is a membrane denaturant that can be controlled by means of light irradiation. Membrane resistance was measured to determine that the photosensitizer, as activated when the entire cell is irradiated with light, raises the membrane resistance, that is, ion permeability of the membrane. The inventors have also clarified that the amounts of light and photosensitizer can be controlled to control a change in membrane resistance caused by light irradiation, to three levels.
1) No effect
2) Recovery after a decrease in resistance
3) Loss of resistance Furthermore, the inventors have found a feature of this method that the ion permeability of the membrane recovers to its state prior to destruction in about 30 seconds under preferred conditions.

A similar change in membrane resistance was observed when only the axon of the cell was irradiated with laser beams.

Furthermore, to determine whether the denaturing of the cell membrane using the photosensitizer is applicable to introduction of a substance to the cell, the inventors attempted to apply it to a microinjection process. For the microinjection process, an injection liquid containing the water-soluble fluorescent dyeing reagent Lucifer Yellow CH (LY) was prepared and whether or not the LY could be injected into the PC12 cell was used as an index for determining whether or not the injection was successful. In addition, an electric manipulator was used to automate the injection process to minimize the artificial effects on evaluation of the success rate.

With this injection process system, measurements were made to determine how the injection success rate varied depending on the presence of 100 $\mu$M of the photosensitive 5'5"-bis(aminomethyl)-2,2':5'2"-terthiophene dihydrochloride in the injection liquid or the presence of a process for irradiating the membrane with light from a 100-W mercury lamp.

As a result, when the injection liquid containing the photosensitizer was used and the light irradiation was executed, the injection success rate was about 80%. In other control examples, the rate was about 0 to 10%. Therefore, membrane denaturing has been confirmed to significantly improve the injection success rate.

Furthermore, using a rate at which the cell retained the LY after the injection process, as an index for a cell survival rate, the cell survival rate was compared between the photosensitive process and the normal process. Photosensitized cells exhibited a survival rate of about 90% for three to six days, which is significantly higher than that of normally processed cells, that is, about 10%.

Thus, the combination of the photosensitizer with light has been shown to serve to appropriately punch the membrane. That is, conditions for repairing the membrane without killing the cells can be easily determined depending on the level of membrane destruction. Of course, it is easy to produce a membrane destroying member with a membrane destroyer such as the photosensitizer applied to a support and then bring the membrane destroying member in contact with the membrane.

The inventors further produced a new member by providing a scanning probe of an atomic force microscope with an electrode and applying 5'5"-bis(aminomethyl)-2,2';5'2"-terthiophene dihydrochloride to a probe section. When the member with this photosensitizer applied thereto is inserted into the cell membrane, resistance originating from the cell membrane is observed between the electrodes located inside and outside the membrane. Since a physical shearing force applied by the electrode of the atomic force microscope is not strong enough to punch the cell, it has been shown that the newly produced member can be used as one acting as the electrodes of the atomic force microscope and providing a controllable membrane destroying function.

Next, the inventors attempted to achieved a spatial resolution of 20 $\mu$m using as an representative example of a nerve interface, one having such a specific target size of its own that it can be applied to mammalian peripheral nerves. The value of 20 $\mu$m was set because peripheral myelinated nerves (A fibers) that carry out normal muscle control and sense transmission have a diameter between 1 and 22 $\mu$m.

The inventors further selected a rate phechromocyte PC12 cell as a nerve model. The PC12 cell was established by Greene and Tischler in 1976 [Proc. Natl. Acad. Sci. USA 73, 2434–2428 (1976)]. This call is characterized to differentiate into a cell similar to a nerve when a nerve growth factor (NGF) is added thereto and is commonly used as a nerve cell model.

To examine a cell membrane penetrating nerve interface according to the present invention, physical conditions such as insertion speed and pressure which are required to insert minute metal electrodes into the cell must be evaluated. As an electrode system that could quantitatively examine these conditions, a scanning probe of an atomic force microscope (AFM) was provided with an electrode and used with the AFM. This system has the following advantages:
1) An image of the cell can be picked up to specify an electrode inserting position.
2) The electrode can be manipulated at a spatial resolution in the order of nanometers.
3) Since the system operates under digital control, electrode connection conditions can be quantitatively optimized.
4) Attempts can be made to automatically connect the cell and the electrode together by controlling the positions of the electrode based on program operations.
5) A probe section of a commercially available ATM probe is shaped like a rectangular pyramid of base and height each 10 $\mu$m, so that the target spatial resolution of the 20 $\mu$m can be sufficient achieved even with modifications required to provide the probe with electrode.

Data obtained by the AFM probe electrode can be used to develop a nerve interface using a membrane-penetrating metal electrode.

This enables membrane potential to be measured by bringing the electrode into close contact with the membrane. To measure a potential in the cell, however, the electrode must be inserted into the cell using a certain method. The conventional method uses a physical shearing force to insert a glass capillary or the like. A major problem with this method, however, is that if the minute electrode is composed of metal, it is support has an insufficient physical strength to penetrate the membrane.

The inventors have thus designed and developed a method for applying a cell membrane destroying technology using a method other than the physical shearing force, to insertion of the electrodes. By way of example, the inventors have succeeded in allowing the electrode to easily penetrate the membrane by coupling an electrode inserting operation to a cell membrane destroying operation using a compound that generates an activated oxygen species.

By way of a specific example, the inventors succeeded in producing an atomic force microscope actually equipped with a cell membrane destroying probe electrode, selecting an electrode installing portion while measuring the shape of a surface of the cell, and then inserting the electrode into the cell membrane. Those skilled in the art can integrate a number of electrodes together as appropriate using the above single electrode as a prototype.

That is, the present invention includes:
(1) an electrode comprising an insulated support, a conductive pattern formed on a surface of the insulated support, an insulator formed on the conductive pattern in such a manner that a portion on the conductive pattern which comes in contact with at least a membrane after the membrane has been penetrated can be insulated, and a membrane denaturation reaction prompting portion formed in the portion coming in contact with the membrane or in a neighborhood thereof and having a membrane denaturing force other than a physical shearing force, (2) the electrode according to (1), wherein the insulated support comprises a particular support and an insulating layer covering a surface of the support, (3) the electrode according to (1) or (2), wherein a compound that causes the membrane denaturation reaction prompting portion to induce membrane denaturation reaction is applied or fixed to the electrode, (4) the electrode according to (3), wherein the membrane denaturation reaction utilizes a chained peroxidation reaction of membrane components started by a direct or indirect generation reaction of an activated oxygen species, (5) the electrode according to (3) or (4), wherein the membrane denaturation reaction includes a reaction induced by a particular stimulus and a reaction precursor to denature or destroy the membrane, (6) the electrode according to (5), wherein the particular stimulus is light and the reaction precursor is a photosensitizing compound, (7) an electrode according to any one of (1), (2), and (3) to (6), wherein after the membrane has been denatured or destroyed, the electrode penetrates the membrane and the penetrated membrane comes in close contact only with part of the insulating portion, (8) an electrode including a support comprising silicon processed by means of etching, wherein gold (Au) with a thickness of 220 nm is plated on a bottom surface (a measuring surface) of the support, areas of the electrode other than a measuring metal terminal and an equipment-connected metal terminal are insulated and covered by silicon dioxide with a thickness of 100 nm, and 5'5"-bis (aminomethyl)-2,2':5'2"-terthiophene is applied to an electrode section, (9) the electrode according to any one of (1) to (8), wherein the electrode is connected to a position controlling device, and a position where the electrode is inserted into or contacted with the membrane can be controlled,

(10) the electrode according to any one of (1) to (9), wherein the electrode is connected to the position controlling device and has a function for measuring a shape of a surface of the membrane or a solid,

(11) the electrode according to any one of (1) to (10), wherein the insulated support comprises a scanning probe of a scanning probe microscope,

(12) the electrode according to any one of (1) to (11), wherein at least a part of the measuring metal terminal is covered with an insulator membrane or a conductor membrane, and

(13) an interface type minute membrane potential measuring apparatus comprising the electrode and the potential measuring device according to one or more of (1) to (12).

The electrode provided by the present invention comprises the membrane denaturation reaction promoting portion having a membrane denaturing force other than the physical shearing force. Preferably, the electrode is connected to the position controlling device and, more preferably, it contacts therewith at such an arbitrary pressure that a surface of the membrane is not destroyed.

When the electrode is based on a common one including a support, a measuring metal terminal, an insulating portion and can retain electrode functions, it can be composed of common materials. For example, the support may preferably composed of silicon, glass, or the like. The material of the conductive pattern may be gold (Au), platinum (Pt), or other metal generally used for patterning in the field of electronics. An example of the insulator used in the insulating portion includes silicon dioxide or silicon nitride. The electrode may have additional functional, for example, an electrode position indicating function based on a fluorescent coating or an extended lifetime resulting from coating with an antiseptic unless the electrode functions are degraded.

The membrane denaturing portion of the electrode having the membrane denaturation reaction promoting portion refers to a portion that comes in contact with a particular portion of the membrane which is denatured or destroyed. The membrane denaturation reaction may be a chemical reaction including a reaction using radiation, laser beams, or the like, an enzymatic reaction using lipase or protease, or a chained peroxidization reaction of membrane components started by a direct or indirect generation reaction of an activated oxygen species. An example of the chained peroxidization reaction includes a lipid peroxidization reaction of a living membrane, and, more specifically, includes generation of a radical, singlet oxygen, superoxide, or generation of hydrogen peroxide.

Although the electrode does not necessarily require a substance causing the membrane denaturation reaction to be applied or fixed to the membrane denaturation reaction prompting portion if radiation or the like is used, it may have a compound applied or fixed to a portion thereof, the compound including an enzyme or a compound that involves generation of activated oxygen and causing the membrane denaturation reaction. Preferably, the applied or fixed compound is a reaction precursor that causes the membrane denaturation reaction when subjected to a particular stimulus. An example of the combination of the "particular stimulus" and the "reaction precursor" includes "light" and a "photosensitizer" for a light-induced electron transfer reaction, "radiation" and a "cell membrane and moisture molecules" for a radiative chemical reaction", or a "change in electrode potential" and a "conductive polymer" for an electrode reaction.

More specifically, the photosensitizer that promotes generation of singlet oxygen when irradiated with light includes methylene blue, rose bengal, chlorophyll (a common name), hematoporphyrin, posoralen, bilirubin, riboflavin, chlorophyll, or retinal, and the compound that generates activated oxygen on the electrode upon application of a potential includes methylviologen. An example of the conductive polymer that is radicalized on the electrode when provided with a potential includes polyacetylene or polythiophen. A thiophen trimer (terthienyl) is a natural photosensitizer obtained from a plant and can be used as a compound that can induce membrane destruction upon application of light or a potential. The compound that catalyzes radicalization when irradiated with light may be semiconductor particles such as a ruhtenium (II) trisbipyridine complex or titanium oxide, or a starting agent that starts radical polymerization when irradiated with light may be used as a photosensitizer. For example, the photopolymerization sensitizer based on irradiation with ultraviolet rays may be a peroxide such as a benzoyl peroxide, an azo compound such as azobisisobutyronitryl, a carbonyl sulfur compound such as diacetyl, dibenzyl, etc. diphenyl monosulfide, diphenyl disulfide, dibenzoyl monosulfide, or dibenzoyl disulfide, a halogen compound such as $CCl_4$, and a metallic salt such as $FeCl_3$.

If the level of membrane destruction based on lipid peroxidizing cannot be easily controlled based only on the quantitative ratio of the "particular stimulus" and the "compound activated by a stimulus" or the like, the level of destruction may be controlled by adding a substance such as lipid or an oxidation inhibiting substance that weakens the lipid peroxidization reaction or assists membrane repairs.

Depending on the level of membrane denaturation, the electrode having the membrane denaturation reaction promoting portion as described above may contact with the membrane so as not to completely destroy it or may be used in such a manner that after the membrane has been denatured or destroyed, the electrode penetrates the membrane, which comes in close contact only with part of the insulating portion.

A specific example is an electrode including a support comprising silicon processed by means of etching, wherein gold (Au) with a thickness of 220 nm is plated on a bottom surface (a measuring surface) of the support, areas of the electrode other than a measuring metal terminal and an equipment-connected metal terminal are insulated and covered by silicon dioxide with a thickness of 100 nm, and 5'5"-bis(aminomethyl)-2,2':5'2"-terthiophene is applied to an electrode section.

For the former type of electrode, that is, the electrode having the membrane denaturation reaction promoting portion, and the latter type of electrode, that is, the electrode connected to the position controlling device and which can contact with the surface of the membrane at such an arbitrary pressure that the membrane is not destroyed, both types of electrodes may be connected to the position controlling device to control the position where the electrode is inserted into or contacted with the membrane or may have a function for measuring the shape of the surface of the membrane or a solid, or may be a scanning probe of the scanning probe microscope.

In addition, both electrode can preferably be used even if at least part of the measuring metal terminal is covered with an insulated or genetic film, unless the electrode functions are lost. Further, an interface type minute membrane potential measuring apparatus can be provided which includes a combination of a plurality of the above-described electrodes and a potential measuring device. This interface type minute membrane potential measuring apparatus can also be provided as a composite interface type minute membrane potential measuring apparatus including an additional normal electrode or normal metal terminal, or a combination with another potential measuring terminal.

Alternatively, all the above-described electrodes or potential measuring devices can be used as nerve interfaces having the electrode connected to the individual nerve to transmit information between electric information equipment and the nerve, so that they can each be provided as part of precision equipment for use in research such as basic analysis and research on the brain, clarification of living cell mechanisms, or analysis of functional electric stimuli. Each of them can also be used as part of a highly integrated and very accurate invasive measuring type medical electrode or part of a connection and control device for living function substituting and supporting equipment such as an artificial organ. Any of the above-described electrodes or potential measuring devices can alternatively be used for part of a connection and control device for an artificial hand or leg comprising a joint or a sensory organ that can be controlled as in human bodies, or as part of a connection and control device between an artificial sensory organ (a visual or auditory sense) and a living body. Any of the above-described electrodes or potential measuring devices can alternatively be used as a part of a brain function expanding apparatus for patients who have their brains damaged due to the Alzheimer's disease or the Parkinson's disease or as a part of a living function expanding apparatus for recovering a living function lost due to a congenital disease. Communication among living things may be extended by connecting the above-described interface type minute membrane potential measuring apparatus using the electrode not only to human beings but also to general animals or even plants to clarify living information processing mechanisms.

BEST MODE FOR CARRYING OUT THE INVENTION

The present invention will be specifically described below with reference to examples but is not limited thereto.

EXAMPLE 1

Culturing Nerve System Established Cell Line PC12

An established nerve system cell line PC12 as ganglion-like cells obtained from the adrenal medulla of a rat and which are used as a model of the central nerve. A neurobasal medium (manufactured by GIBRO BRL) (pH 7:3) containing 10% of thermally inactivated equine serum, 5% of bovine fetus serum, 7.35 mg/l of L-glutamic acid, and 2 mM of L-glutamine was used to culture PC12 cells in an atmosphere containing 95% of $CO_2$.

The cells were subcultured by spraying a culture medium on the cells, peeling off the cells from a wall surface of a culture flask, centrifuging this 380-g flask for 5 minutes to bias the cells, scattering the cells into a culture flask of base area 25 $cm^2$ (manufactured by IWAKI GLASS Co., Ltd.) for 1 to $3 \times 10^4$ cells/$cm^2$ per ml, and changing the culture medium at the intervals of two or three days.

To differentiate the PC12 cells into nerve-like cells, 2.55 of a mouse nerve growth factor (NGF) was added to the culture medium so that its final concentration reached 50 ng/ml. The solution with the NGF (Marine; 2.5S) dispersed therein, the NGF being added to the culture medium, was prepared as follows:
1) phosphate buffered saline PBS; it was composed of 2.10 g/l of $KN_2PO_4$, 90.00 g/l of NaCl, 7.26 g/l of $NaHPO_4$, $7H_2$, and a 1-N NaOH solution, with a pH adjusted to 7.4) was provided.
2) Two mg of bovine serum albumin (NSA) was dispersed in 1000 μl of the above-described PBSI (with a pH adjusted to 7.4), and the dispersed solution was passed through a filter of pore size 0.22 μm for sterilization.
3) One hundred μl of the sterilized solution and 100 μg/ml of NGF solution (commercially available from GIBCO BRL) were added together to obtain a total amount of 200 μl. The solution were dispensed into different mini-tubes so that each mini-tube contained 8 μl of the solution. The mini-tubes were then frozen and stored at –20° C.

The NGF solution dispensed in this manner was added to a culture medium so as to reduce the concentration to 1/1,000, thereby differentiating the PC12 cells.

The PC12 cells were allowed to adhere lightly to a wall surface of a plastic bottle, where they were grown while forming a small cluster. To culture the cells differentiated into nerve cells, collagen coat dishes (IWAKI Glass Co., Ltd.) were used.

Cells that spent 6 days or more after they had started differentiating into nerve-like cells were used in the following electrophysiological experiments.

EXAMPLE 2

Synthesizing Bisaminomethylterthiophene

Figure 1:
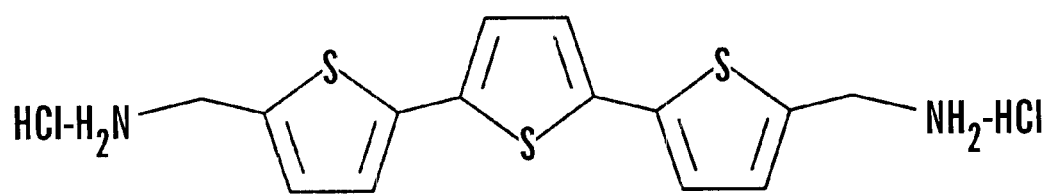
FIG. 1 shows a structural formula of a 5'5"-bis (aminomethyl)-2,2':5,'2"-terthiophene dihydrochloride (BAT) dichloride salt.
Figure 2:
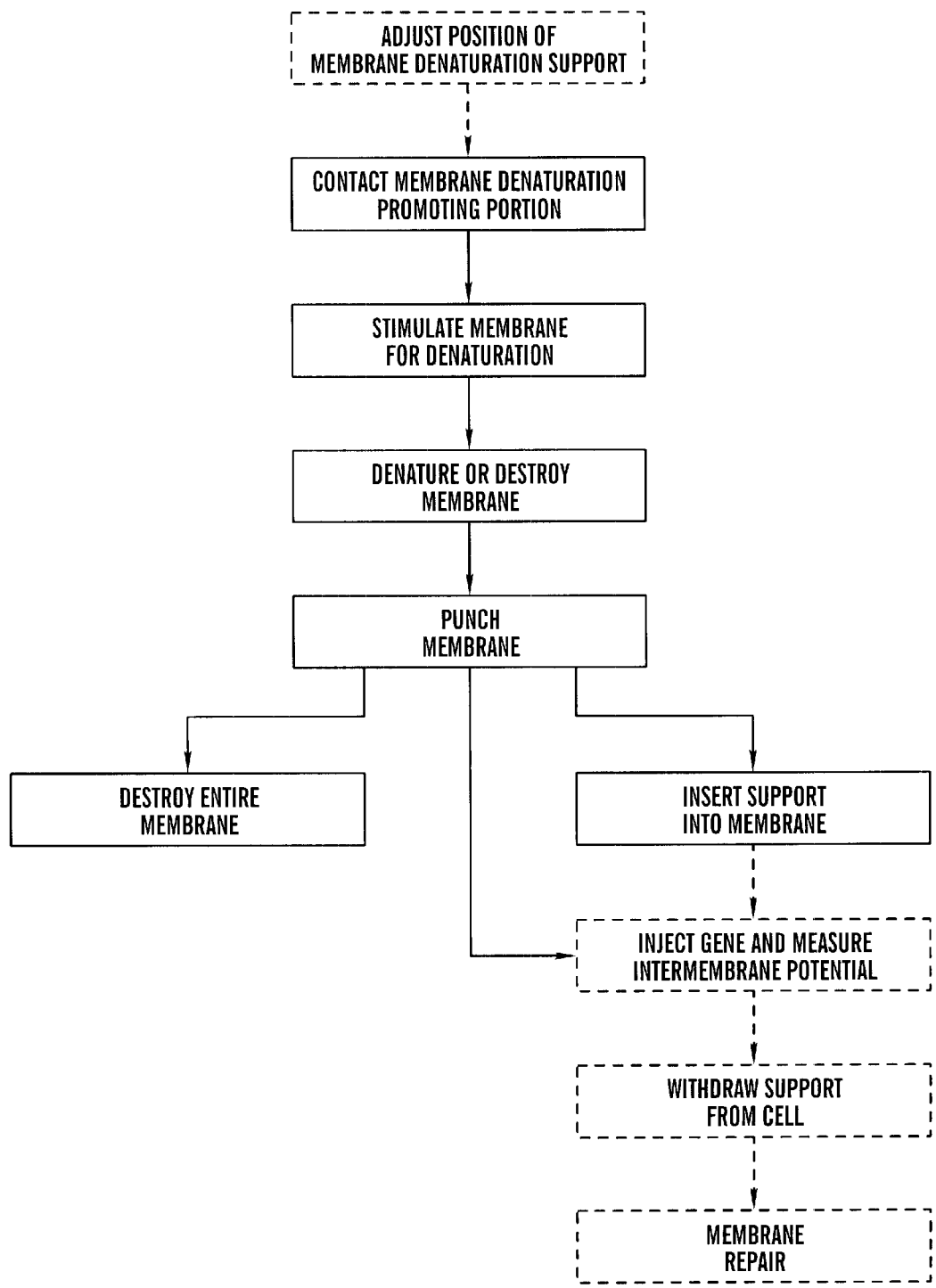
FIG. 2 shows a membrane punching technique flow chart.
Figure 3A:
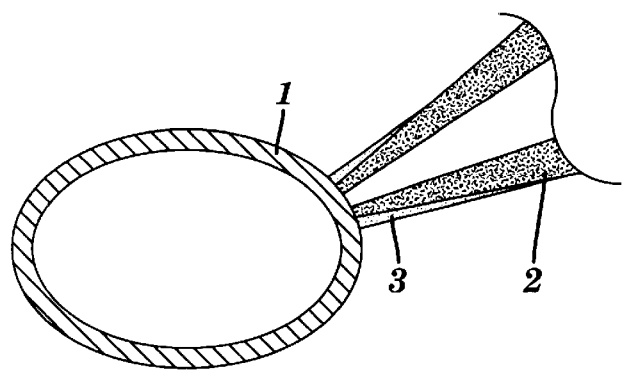
FIGS. 3A–3D show the relationship between a membrane destroying member having a cylindrical support and a membrane structure that is to be processed by the membrane destroying member.
Figure 3B:
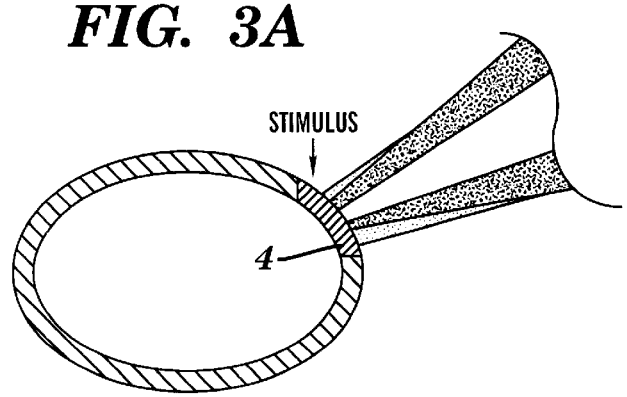
Figure 3C:
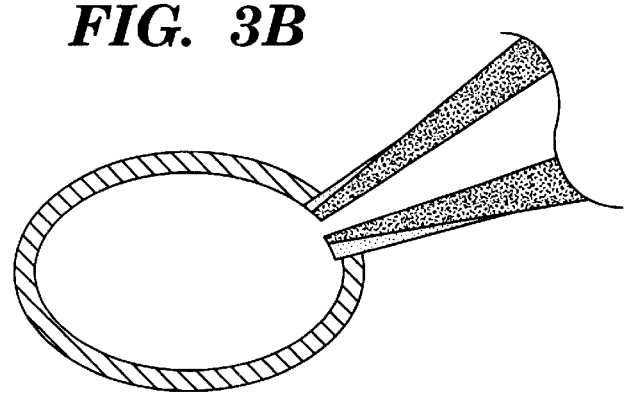
Figure 3D:
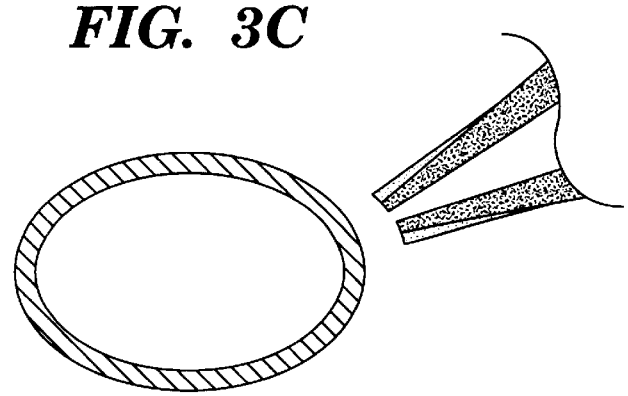
Figure 4A:
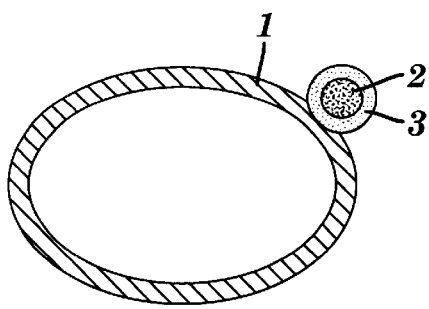
FIGS. 4A–4D show an example of the relationship between a membrane destroying member having a sphere- or bead-shaped support and a membrane structure that is to be processed by the membrane destroying member.
Figure 4B:
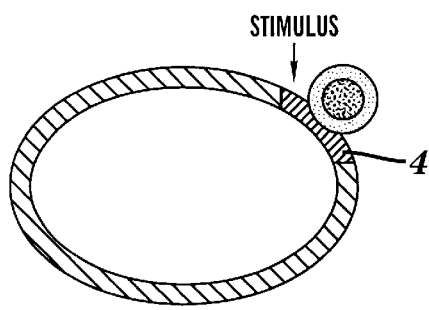
Figure 4C:
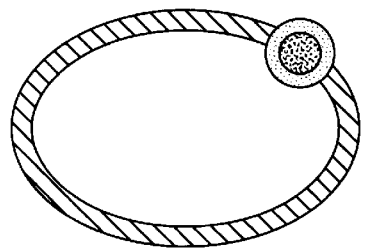
Figure 4D:
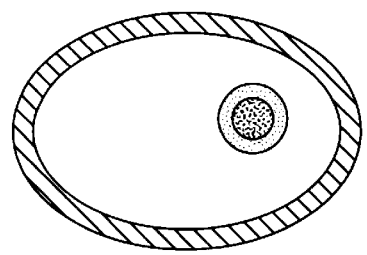
Figure 5A:
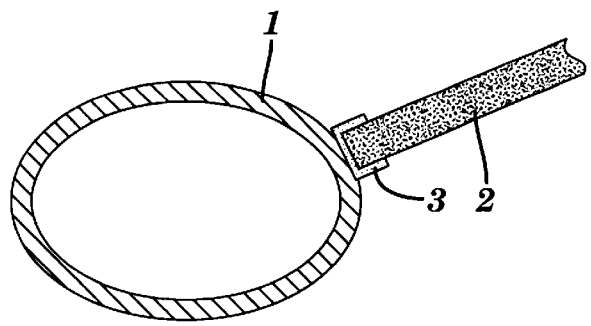
FIGS. 5A–5D show an example of the relationship between a membrane destroying member having a rod-shaped support and a membrane structure that is to be processed by the membrane destroying member.
Figure 5B:
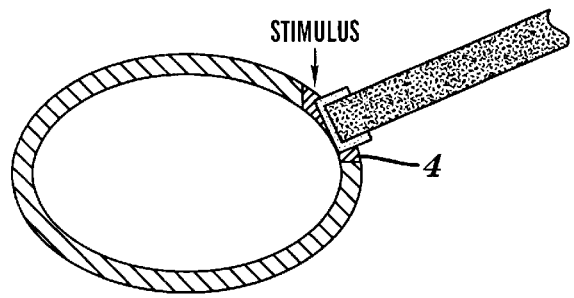
Figure 5C:
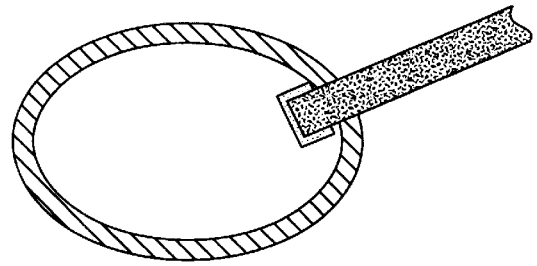
Figure 5D:
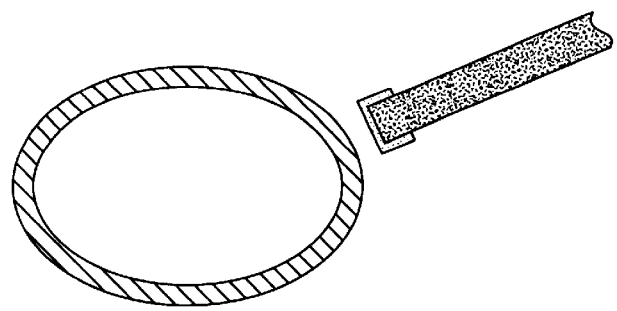
Figure 6A:
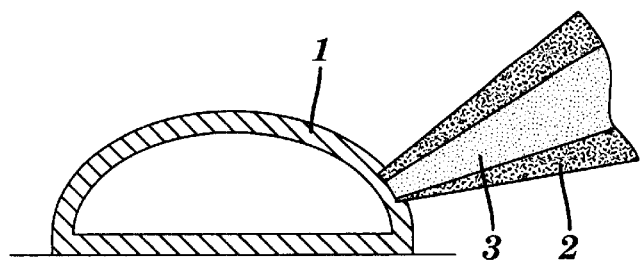
FIGS. 6A–6D show an example of relationship between a cylindrical membrane destroying member having a support for holding a liquid containing a membrane denaturation reaction promoter and a membrane structure that is to be processed by the membrane destroying member.
Figure 6B:
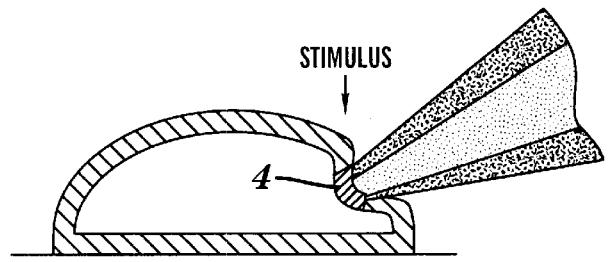
Figure 6C:
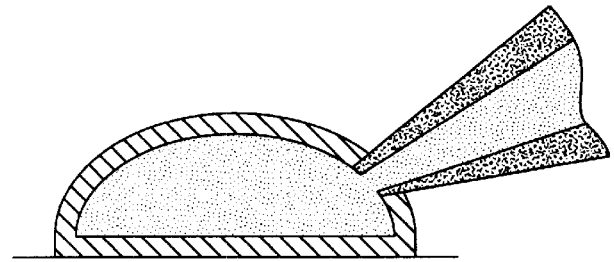
Figure 6D:
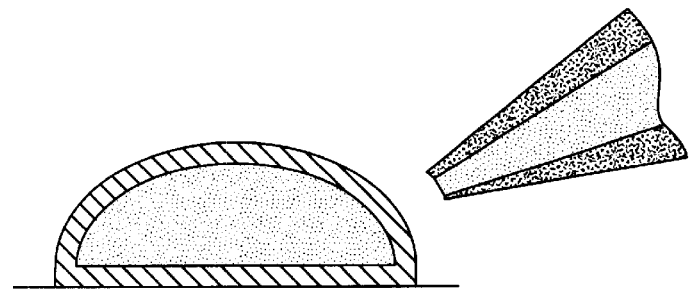
Figure 7A:
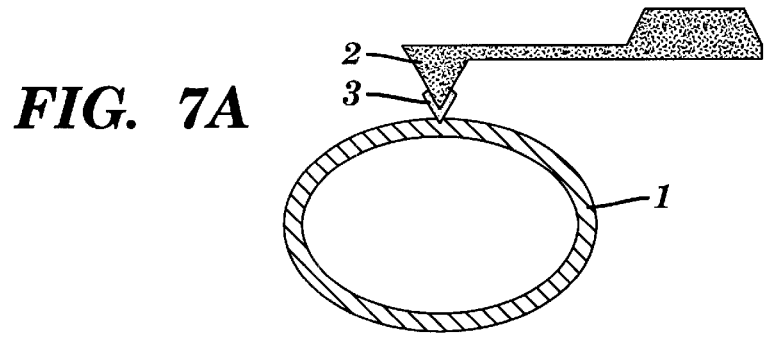
FIGS. 7A–7D show an example of relationship between a member destroying member having a support shaped like an atomic force microscope probe and a membrane structure that is to be processed by the membrane destroying member.
Figure 7B:
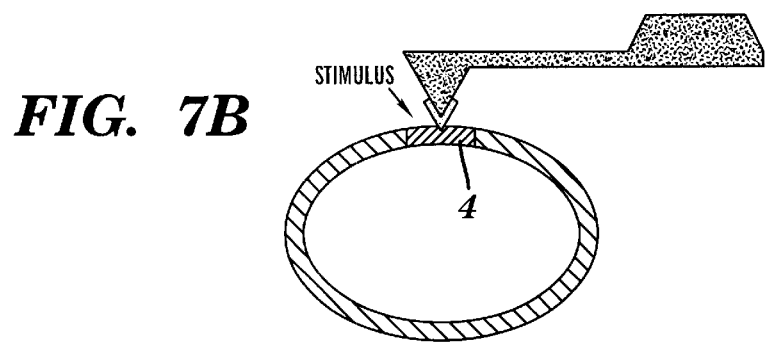
Figure 7C:
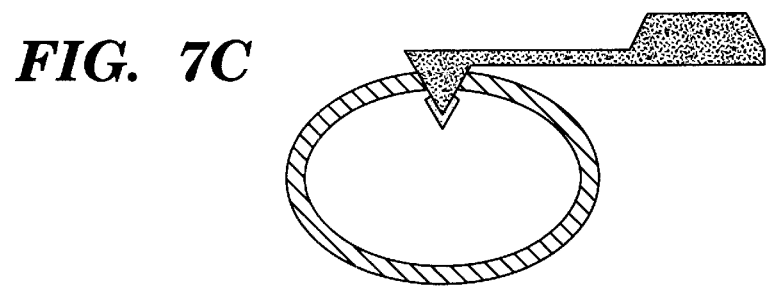
Figure 7D:
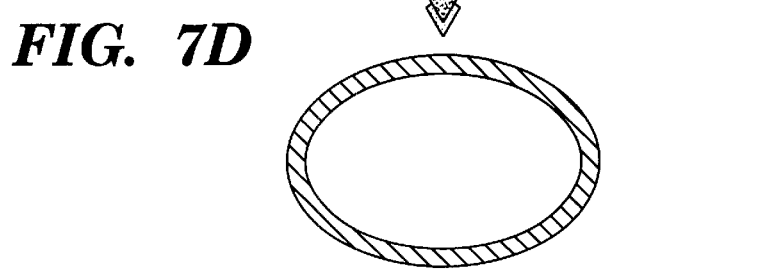
Figure 8:
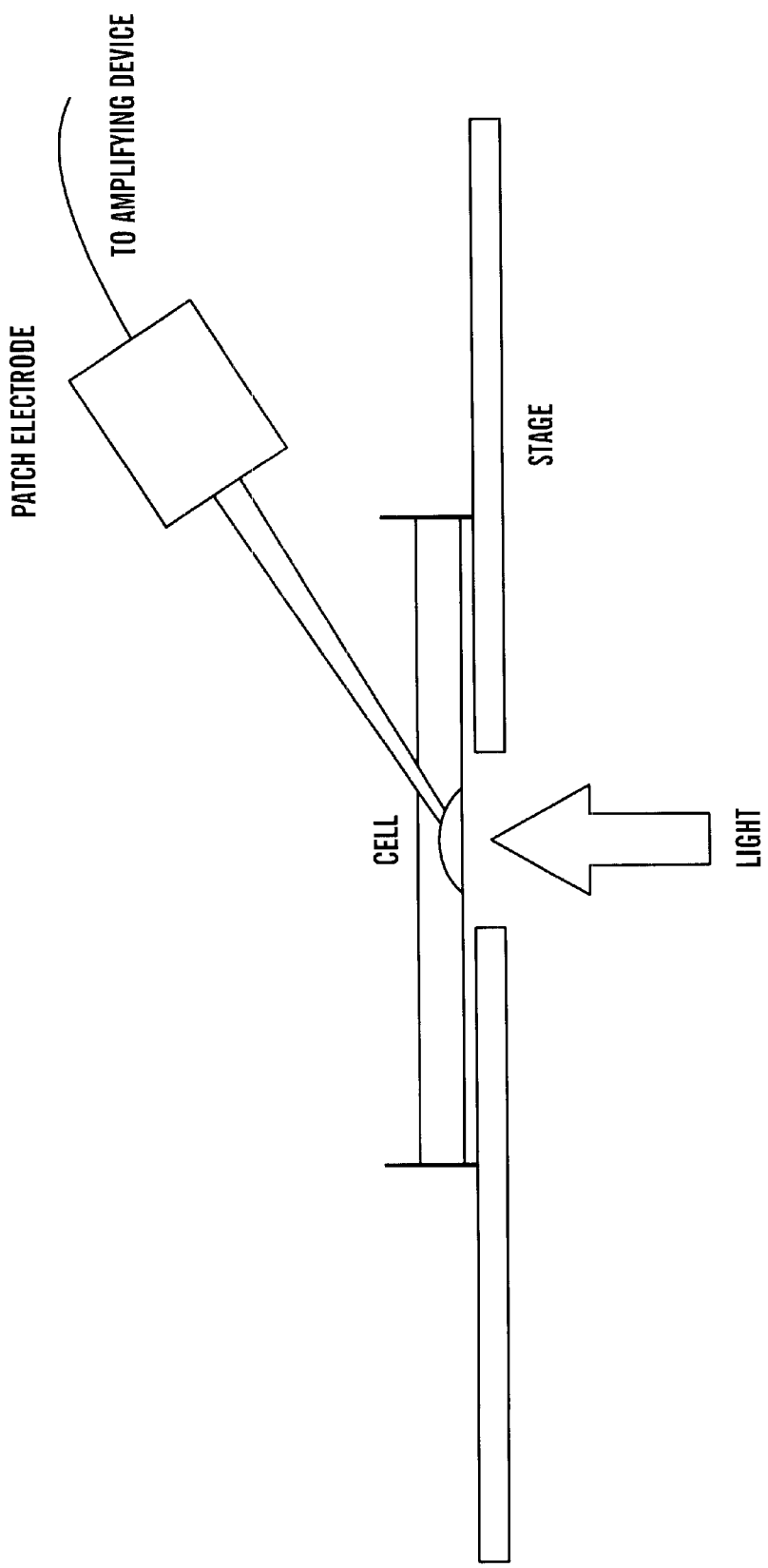
FIG. 8 schematically shows an apparatus for measuring intracellular potential and membrane resistance using a patch electrode.

The pnotosensitizer was composed of 5'5"-bis (aminomethyl)-2,2':5'2"-terthiophene dihydrochloride (BAT), which is an α terthienyl derivative. This compound was synthesized in accordance with the article of Muguruma [J. Hetercyclic Chem., 33, 1–6 (1996)]and provided in a state of BAT dichloride salt. FIG. 1 shows a structural formula for a BAT dichloride salt.

A thiophen oligomer having an aminomethyl group at a terminal thereof has a higher water solubility than any other derivative of the same kind due to this terminal aminomethyl group. The water solubility varies depending on how the aminomethyl group is released. On the other hand, the present BAT is characterized by having two types: one of them has a bivalent positive charge in an acid water solution and is easily soluble therein, while it has a univalent positive charge in a water solution with a biologically suitable pH range (near 7.4) and maintains a high water solubility; the other exhibits the same characteristic in the former solution but in the latter solution, has no charge and is likely to cohere into a colloid. By irrigating the cell with the BAT-dispersed solution under the above pH condition, this molecule can be easily added to a surface of the cell. The hydrophilic property of the BAT molecule is new and is absent from the other modified thiophen oligomers including an a terthienyl derivative as well as other molecules designed as conductive high-molecular monomers.

EXAMPLE 3

Measuring Membrane Resistance and Membrane Potential After Light Irradiation

Since minute membrane defects must be monitored at a cell level for a period of time in the order of seconds to several minutes including a recovery process, the patch clamp method, which is used for electrophysiological experiments, was used to measure the potential between the cell membranes or ion current transmitted through the cell membrane.

The photosensitizer BAT was dispersed in a HEPES (25 mM, pH 7.4) buffer. A dispersed solution to be locally added to a neighborhood of the cell using a micropipette had a BAT concentration adjusted to 2 mM, and a dispersed solution to be added to the entire irrigation liquid had a BAT concentration adjusted to 0.2 mM.

The cells were incubated in a culture medium for electrophysiological experiments at roam temperature. The culture medium used for this experiment was composed of 124 mM of NaCl, 5 mM of KCl, 2.4 mM of $CaCl_2.2H_2O$, 1.3 mM of $MgSO_4.7H_2O$, and 10 mM of glucose, with a final pH adjusted to 7.4 by addition of NaOH. To prevent the averse effects of evaporation, the culture medium for electrophysiological experiments was replaced with a new at the intervals of 40 minutes at maximum.

The BAT was added so as to have a final Concentration of 49 μM. The quantity of light applied was set at three levels: 0.47 $J/cm^2$, 0.94 $J/cm^2$, and 1.57 $J/cm^2$.

A liquid in the patch electrode was composed of 132 mM of KCl, 8 mM of NaCl, 2 mM of $MgCl_2$, 30 mM of HEPES, 4 mM of $Na_2ATP$, 0.3 mM of GTP, and 0.5 mM of EGTA, with a final pH adjusted to 7.3 by addition of NaOH.

An excitation light source was a 50-mW and 363-nm argon ion laser including a confocal laser scanning microscope (CLSM) MRC-1000 UV (BIO-RAD laboratories) as standard equipment. one-sixteenth (¼ along each of thexand Y axes; 117×170 μm) of the full screen (about 470×680 μm of the microscope was scanned by the laser beams. This area was set to cover the entire patched target cell. The laser beams had a 100% output of 50 mW. The amount of irradiation time was selected from ¹⁄₁₆, ¼, and ¹⁄₃₂ seconds depending on a scan speed. A filter was also used to reduce the amount of light. Since a zoom function allows light to be concentrated in an area smaller than a normal area, the amount of light per unit area increases in proportion to the square of a zoom magnification. The excitation light is transmitted through the plastic of the collagen coat dish before actually reaching the cell, so that a decrease in light quantity must actually be taken into consideration.

In irradiating the cell with the excitation light, a TTL signal operating in connection with an electrophysiological record is transmitted to the light source as required to synchronize the light irradiation with electric measurements.

Before starting the electrophysiological experiments, the cell membrane potential had been maintained between –80 and –60 mV. The patch electrode had a resistance between 3 and 4Ω and was filled with the above-described intraelectrode liquid.

The cell membrane potential measuring amplifier was Axpopatch 1-D (Axon Instruments). The membrane resistance was calculated from a change in membrane potential occurring when a 1-Hz rectangular-wave overpolarization current flowed through the membrane for 350 milliseconds. The amount of, current supplied (0.1 or 0.15 nA) was selected so that the change in membrane potential would not exceed 30 mV when power was supplied. Under these experimental conditions, the PC12 cell generated no action potential. Measured potential and current values were analyzed using Axoscope ver. 1.1 (manufactured by Axon Instruments). Results are shown in FIG. 9.

Figure 9A:
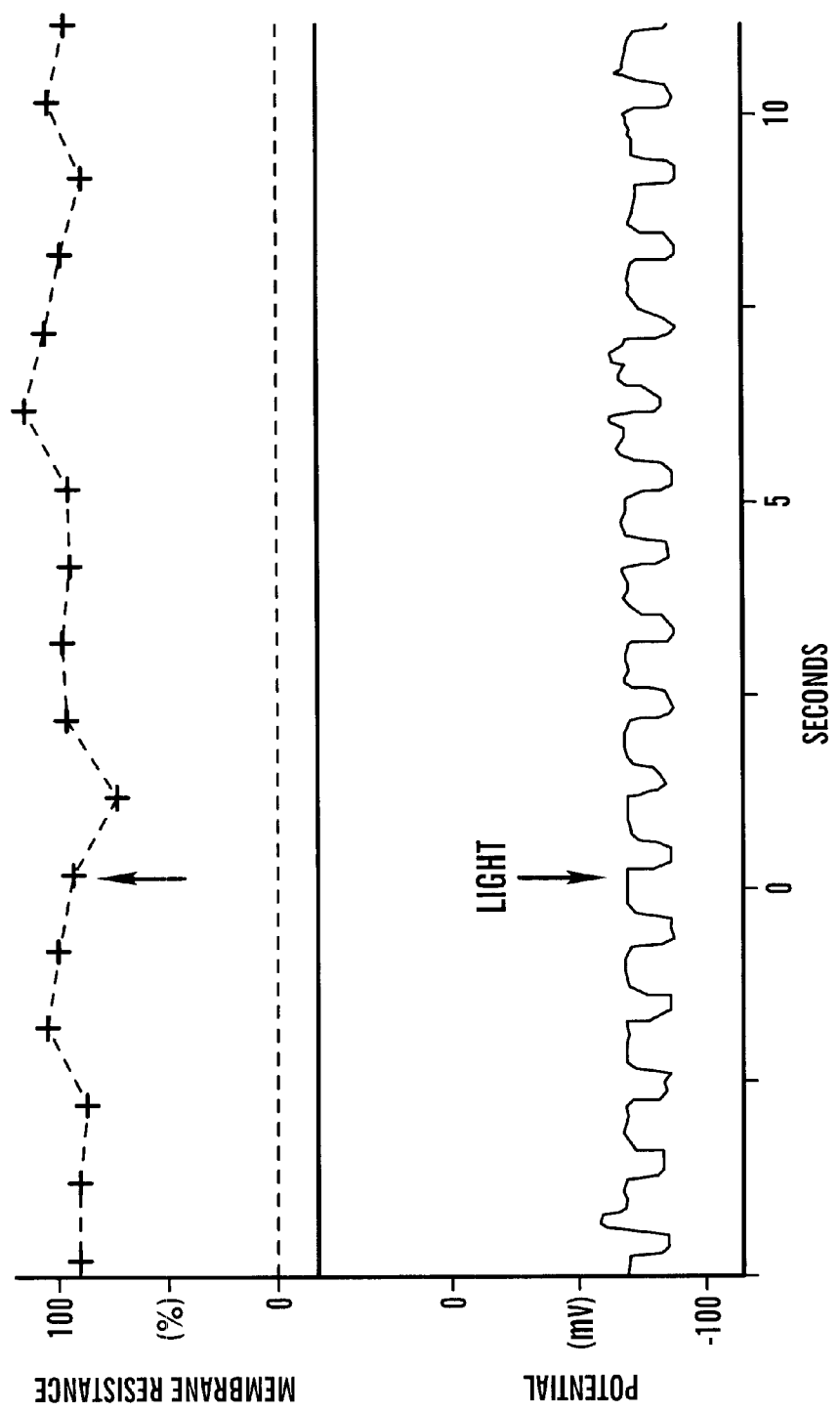
FIGS. 9A–9C are graphs representing the relationship between the intensity of a light stimulus and variations in cell membrane potential or membrane resistance.
Figure 9B:
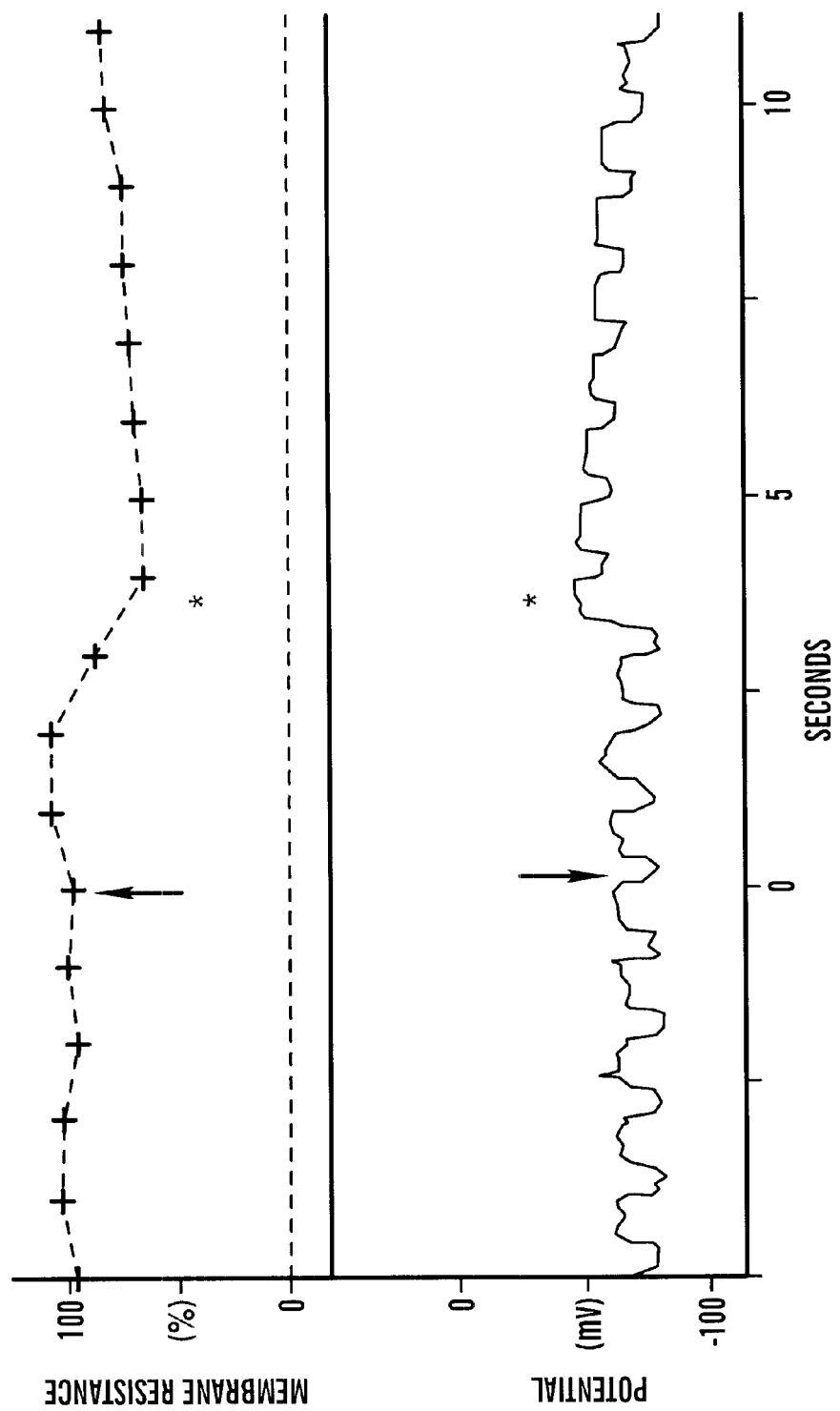
Figure 9C:
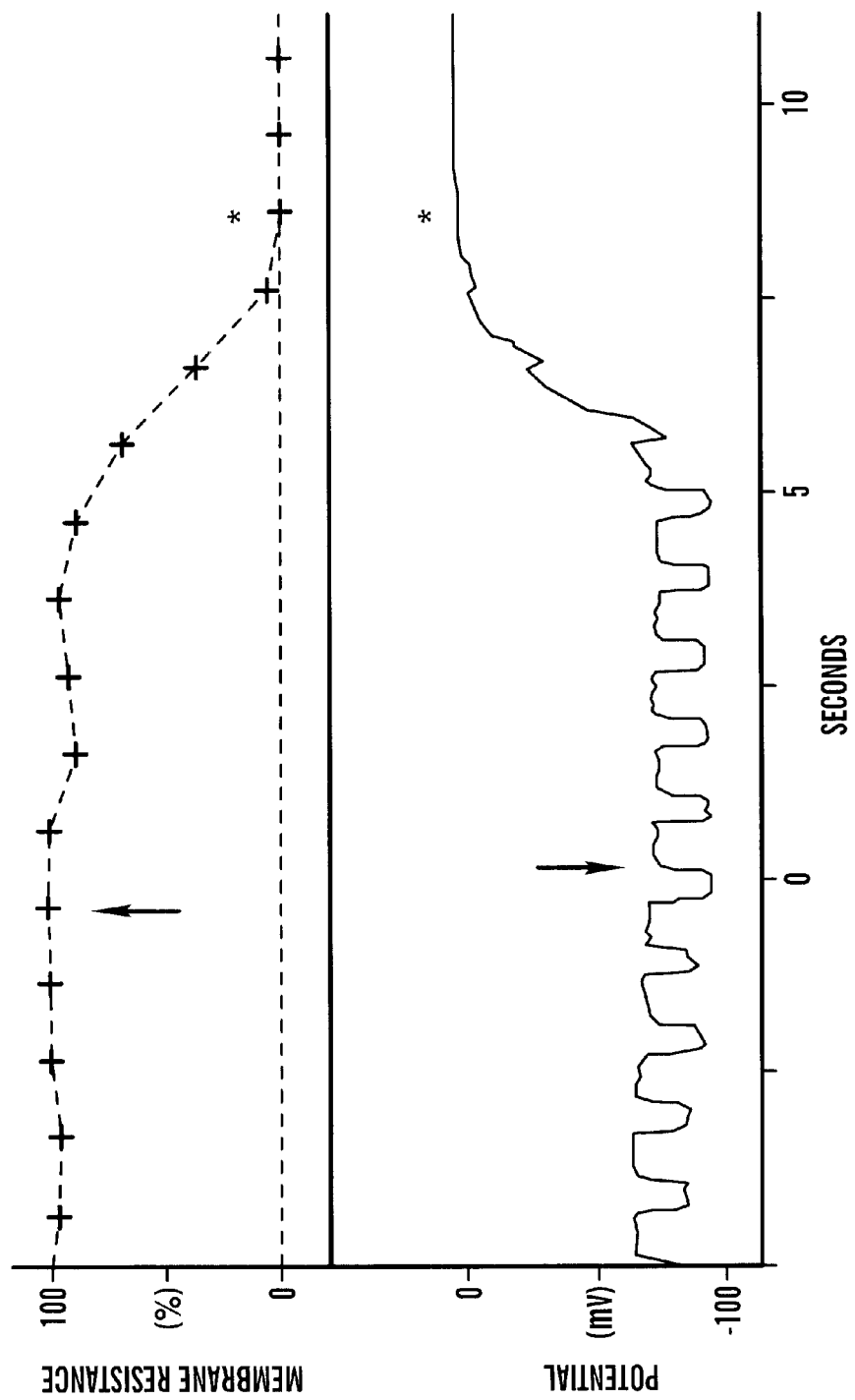

In FIG. 9, the axis of abscissa indicates an elapsed time (unit: second). The axis of ordinate indicates the resistance of the cell membrane (unit: %) in the upper part and the potential thereof in the lower part, both values being normalized by setting corresponding values prior to irradiation equal to 140. The membrane resistance reflects the ion transmission inhibiting capability, and the membrane potential reflects the active ion transporting capability of the membrane effected by activities of various intermembrane ion transporting systems as well as the ion transmission inhibiting capability.

The amount of light applied was smallest for A (0.47 $J/cm^3$), the second smallest for B (4.94 $J/cm^2$), and the largest for C (1.57 $J/cm^2$). For A, both cell membrane resistance and membrane potential varied slightly but not significantly after the light irradiation. For B, the cell membrane resistance decreased and the membrane potential was depolarized several seconds after the light irradiation; this amount of time corresponds to an induction period. Under these conditions, the resistance and potential were also observed to recover to the corresponding values prior to the light irradiation 30 minutes later. This is because, after destruction, the membrane was repaired due to a biological reaction. For C, the cell membrane resistance and membrane potential were lost several seconds (also corresponding to an induction period), that is, about 8 seconds after the light irradiation and then remained at fixed values. This is because no repair reaction occurred after the membrane was destroyed, that is, irreversible membrane destruction occurred.

EXAMPLE 4

Spraying BAT on Target Cell using Minute Glass Pipette

A microinjection device was connected to a minute glass pipette held in a micromanipulator, and the minute glass pipette was filled with a solution with the photosensitizer BAT dispersed therein (BAT concentration: 2 mM, water solvent). The glass pipette was located in such a manner that its tip was connected to the patch electrode and located within 200 μm from a cell for which the membrane potential and resistance were to be measured. The minute glass pipette was pressurized to eject the BAT-dispersed solution, so that the BAT adhered to a target cell membrane. when a laser beam was applied to the cell as in Example 3, the cell membrane potential was observed to be depolarized,

EXAMPLE 5

Microinjection Process using Portion-Specific Membrane Destruction

An operation of introducing a substance using membrane destruction was applied to a microinjection process.

To determine whether the microinjection process was successful, the water-soluble fluorescent pigment Lucifer Yellow CH (LY)was added to an injection liquid. After the injection process, this process was determined to be successful when a LA—induced yellow fluorescence was observed in the cell through a fluorescence microscope. Evaluation was made to determine how the success rate of injection of the LY into the cell varied depending on the presence of the photosesirizer BAT in the injection liquid or the presence of application of the BAT exciting light.

The LY is a less toxic fluorescent pigment used for microinjection and is characterized by shifting to a daughter cell upon cell division [Cell & Tissue Res., 234, 309–318 (1983)]. The LY is so water soluble and dispersible that it is also used as cell fluorescent label agent for the nerve system [Cell & Tissue Res., 254, 561–571 (1988)]. The LY is also characterized by shifting fast in several minutes between cells coupled together by means of a gap junction ["New Physiological System 7, Physiology for Generation and Differentiation, Chapter 4, Generation of Intercell Coupling, I. Electric Coupling", Medical Publishing Company (1991)], which is a liquid-liquid junction the between cells. There has been a report describing the use of the PC12 as a marker for forming a gap junction [J. Neurosci., 14, 3945–3957 (1994)]. A cell with the LY injected thereinto may be killed when irradiated with an excessive amount of LY exciting light [Science, 206, 702–704 (1979)]. Comparison and evaluation were made to determine how the success rate of injection into the cell varied depending on the presence of the photosesirizer HAT in the injection liquid or the presence of application of the HAT exciting light.

To make the microinjection successful, a glass capillary having a diameter of several hundred nanometers at a tip opening thereof must be brought into contact with the cell at a high speed to physically instantaneously penetrate and punch the cell membrane. In the experiments, an electric micromanipulator (manufactured by Eppendorf; Micromanipulator 5171) and an electric injector (manufactured by Eppendorf; Transjector 5246), which can both operate under the control of a program, could be used to set a speed at which the capillary contacted with the membrane, at an arbitrary value. In addition, the injection capillary was a commercially available product (manufactured by Eppendorf; FemtoTips) mass-produced for the above apparatuses. Since the electric micromanipulator served to automate the injection operation to achieve a high reproducibility and the commercially available capillary was used, which is more uniform in shape than those made by the inventors, a statistical process could be carried out for the injection success rate. The micromanipulator was installed in the fluorescent microscope (manufactured by Olympus Optical industry Co., Ltd. according to a specification for an IX70 fluorescent microscope). The light source for exciting the photosensitizer was an ultraviolet light obtained by transmitting light through an ultraviolet exciting filter set (manufactured by Olympus Optical Industry Co., Ltd.; a U-MWU mirror unit), the light being emitted from a 100-W mercury lamp that was an epifluorescent light source built into the microscope. An area covered by the applied light was a circle of diameter 100 μm, which was set using a diaphragm of a fluorescent optical system of the microscope. The LY exciting light source for determining whether the LY was successfully injected into the cell was a violet light obtained by transmitting light from the 100-W mercury lamp through a violet light exciting filter set (manufactured by Olympus Optical Industry Co., Ltd.; a U-MWBV mirror unit) as described above.

With this system, the photosensitizer BAT was concentrated in the area of diameter 0.5 $\mu$m, while it was promptly diluted due to dispersion in areas other than the one contacted with the capillary. Thus, in the capillary-contacted portion, the photosensitizing effect of the BAT is equal to that of 100

C4M BAT in the injection liquid. In terms of the effects of the BAT concentration on the cell, compared to the BAT concentration in the portion of the cell contacting with the capillary, the BAT concentrations in the other portions are negligible.

For the injection operation, the operational range of the manipulator was set so that the capillary could be stuck into the cell at a capillary contact speed of 1,000 $\mu$ms$^{-1}$ the capillary was then operated at a low speed of 7 $\mu$ms$^{-1}$ to come in contact with the cell membrane so as not to physically punch the cell membrane. Under these conditions, comparison was made to determine how the success rate of injection into the cell varied due to the BAT-induced photosensitizing effect.

The photosensitizes BAT was synthesized and provided by Muguruma et al. The reagents listed below were used far the experiments and were commercially available: sodium chloride (NaCl; manufactured by Rishida Chemistry Co., Ltd.), potassium chloride KCl, manufactured by Rishida Chemistry Co., Ltd.), disodium hydrogenphosphate ($Na_2HPO_4$; manufactured by Wako Pure Chemical Industires Co., Ltd.), dipotassium hydrogenphosphate ($KH_2PO_4$; manufactured by Wako Pure chemical Industires Co., Ltd.), and fluorescent marker Lucifer Yellow CH, Lithium salt (LY, ex. 482 nm, em. 536 nm; manufactured, by Molecular Probes).

Each component of the injection liquid was dissolved into pure water so as to prepare a composition having the following final concentrations: 100 $\mu$m of photosensitizes BAT, 40 $\mu$m of HCl, 2 mM of fluorescent marker LY, 8 g/l of NaCl, 0.2 g/l of KCl, 1.15 g/l of $Na_2HPO_4$, and 0.2 g/l of $KH_2PO_4$.

An injection liquid without the BAT for use for a control process was also prepared.

The injection target cells were the established nerve system cell line P12. These cells were obtained from the Cell Development Hank of the Physical and Chemical Research Institute and cultured in accordance with Example 2. The cells subjected to the injection process were subcultured in 35-mm collagen coated dishes (Iwaki Glass Co., Ltd.) at a cell density of 9,000 cells per dish. The cells were cultured by a carbonate dioxide gas incubator (manufactured by Forma Scientific) in an environment at a temperature of 37° C. and a humidity of 100% and containing 5% of carbon dioxide and 95% of oxygen.

The injection process used Hibernat A Media (Hib-A; manufactured by GIBCO BRL) [NeuroReport, 7, 1509–1512 (1996)]that are Hib-A culture media for the injection process and to which were added 10% of equine serum (manufactured by GIBCO BRL), 5% of bovine fetus serum (manufactured by Mitsubishi Chemistry Co., Ltd.; a serum obtained from a quasi-fetus of a Nakashibetsu cow), 7.35 mg/l of L-glutamic acid (manufactured by GIBCO BRL), and 2 mM of L-glutamine (manufactured by GIBCO BRL). The equine serum was thermally inactivated by heating it at 56° C. for 30 minutes. To prepare this solution, water was used which was purified by a pure-water-manufacturing-apparatus Biocel A10/Elix 10 (manufactured by MILLIPORE).

Figure 10:
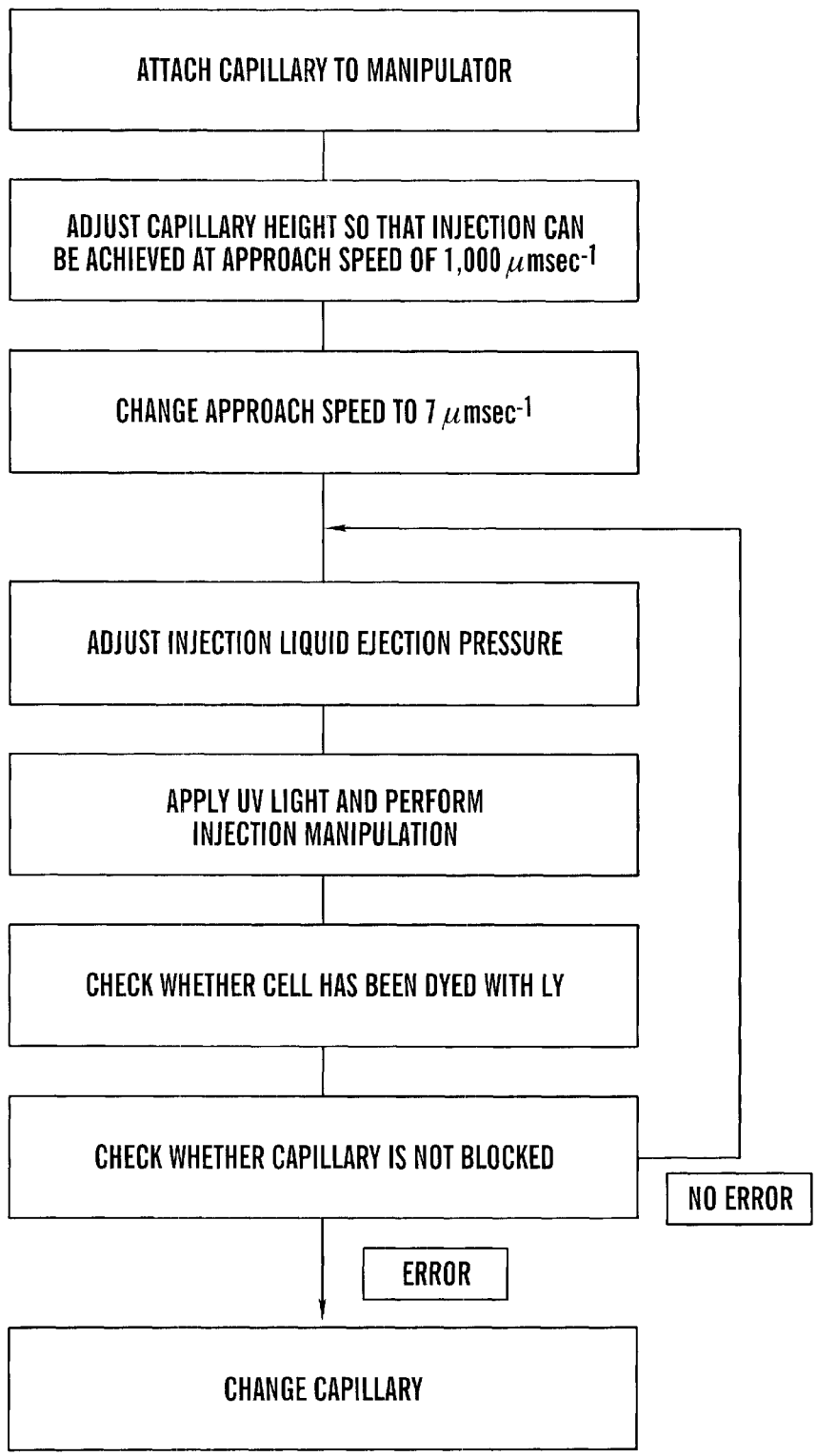
FIG. 10 is a flow chart of an example of photosensitized injection.
Figure 11A:
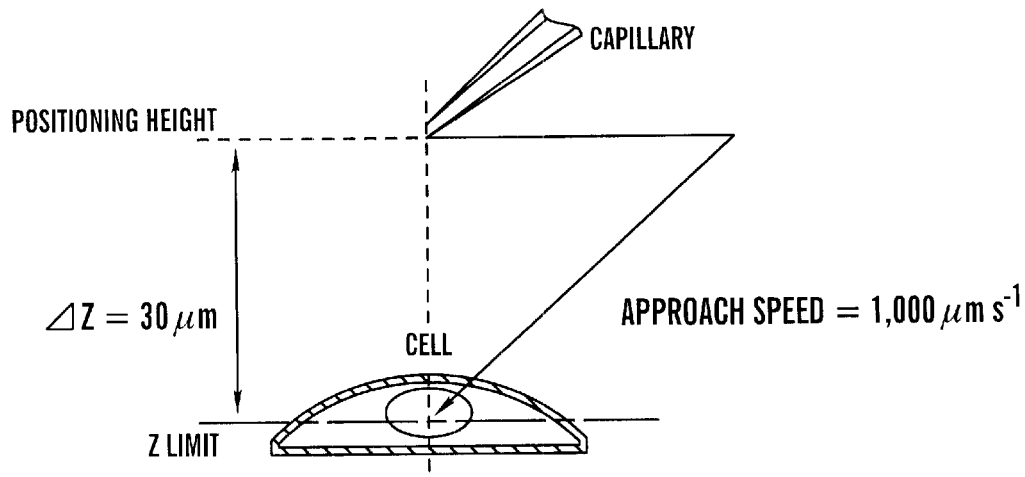
FIGS. 11A and 11B schematically show the example of photosensitized injection.
Figure 11B:
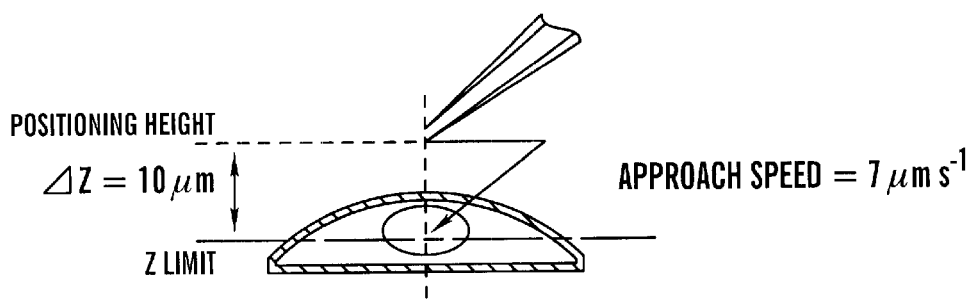

An outline of the injection process procedure is shown in FIG. 10. The following supplement this figure.

1) During the injection process, all of the 3-ml NeuraBasal culture medium was removed from the dish, where the cells had been cultured. The cells on the dish were washed off using 1 ml of Phosphate Buffered Saline, 7.4 (PBS; manufactured by GIBCO BRL) containing neither Ca nor Mg. All the PBS was then removed and 1 ml of fresh PBS was used to similarly carry out washing. All the PBS was removed again, so that the dish was finally filled with 2 ml of the Hib-A culture medium for the injection process. The cells were maintained by this Hib-A culture medium.

2) For this micromanipulator apparatus, a limit position (Z limit) at which the tip of the capillary came closest to a surface of the dish had to be set so that the tip could be stuck into the cell during the injection. The manipulator was set so that the Z limit position aligned with the position of a cell nucleus on the dish.

3) The capillary position was changed to one 30 $\mu$m above the Z limit. The other conditions, that is, an approach speed input value and an injection time were also changed to 700 $\mu$ms$^{-1}$ and 1.1 s, respectively (effective values were 1,000 $\mu$ms$^{-1}$ and 1.0 s, respectively). The z limit position was adjusted so that under these conditions, the normal physical microinjection process could be achieved at a success rate of 80% or more for 10 or more cells. When the success rate was lower, the Z limit position was reset.

4) The capillary position was changed to 10 $\mu$m above the z limit. The approach speed input value and the injection time were changed to 5 $\mu$ms$^{31\ 1}$ and 124 seconds, respectively (the effective value of the injection time was 120 seconds).

5) The epiflourescent light source of the microscope was switched to the violet light exciting (U-MWBV mirror unit) filter set, which is suitable for observing the LY fluorescence A clear function (which presses the injection liquid in the capillary at 7,000 hPa to eliminate blockage from the capillary) of an injector was used to cheek how the LY was ejected from the capillary. When the capillary was found to be blocked, it was replaced with d new one.

6) An injection pressure was set so that the LY was slowly emitted from the capillary tip. The pressure required to allow the LY to be slowly emitted from the capillary tip during the injection process was corrected as required because it varied between 10 and 1,000 hPa depending on the status of the capillary tip. This variation was caused by adhesion of pieces of the cell membrane or minute dirt to the capillary tip. When these substances adhered to the capillary tip, the pressure had to be corrected because the effective amount of ejection liquid emitted varied significantly despite the same pressure exerted on the injection liquid.

7) In a visual field of the microscope, the positions of the cell and the capillary were adjusted so that the capillary tip was located at the center of the cell. To excite the BAT, the epifluorescent light source was switched to the ultraviolet exciting (U-MWU mirror unit) filter set to apply ultraviolet rays. In addition, to suppress the effects of light other than the exciting ultraviolet light, the transmissive light source for observing the cells was interrupted.

8) An injection process switch of the manipulator was pushed. The following process was then automatically executed. The capillary came in contact with the cell, the injection liquid was emitted at that position at the set pressure for the set period of time, and the capillary then returned to the original process.

9) After the injection process, the filter of the epifluorescent light source was switched from the one for ultraviolet light to the one for violet light (U-MWBV mirror unit) to apply the Lx exciting light in order to check whether the cell had been dyed with the LY. If the liquid is injected into a dead cell, the LY leaks quickly from the cell membrane and the fluorescence disappears. Thus, such cells were removed from the data.

10) The transmissive light source for observing the cells was opened again, and the capillary tip was aligned with the next cell while observing the preceding cell.

11) Back to 5), the injection process was repeated. After the injection process, the Hib-A culture medium for the injection process was removed from the dish, and the dish was washed twice using 1 ml of PBS and then returned to the 3 ml of NeuroBasal culture medium. Subsequently, the culture medium was changed in accordance with a normal procedure.

A mixture of antibiotics penicillin and streptomycin, which are antibiotics, was added to the NeuroBasal culture medium after the injection process, in order to prevent the cell culture medium from being contaminated by fungi or bacteria.

To evaluate the success rate of the microinjection using the photosensitizing mechanism, the injection had to be executed under the condition that the physical shearing force of the pipette tip did not contribute to the injection. For an appropriate injection process, the adjustment of the arrival limit position (Z limit) of the capillary is important. Thus, after confirming that an injection success rate of 80% or higher was achieved at the normal approach speed of 1,000 $\mu ms^{-1}$ and with the set Z limit, the approach speed was lowered to 7 $\mu ms^{-1}$. At this approach speed, the capillary tip can reach the same position as in the successful injection, but it hardly penetrates the cell membrane. Under such an approach condition that the membrane could not be punched easily with the physical shearing force, injection success rates obtained using the photosensitizing mechanism were compared together. Results are shown in FIG. 12.

Figure 12:
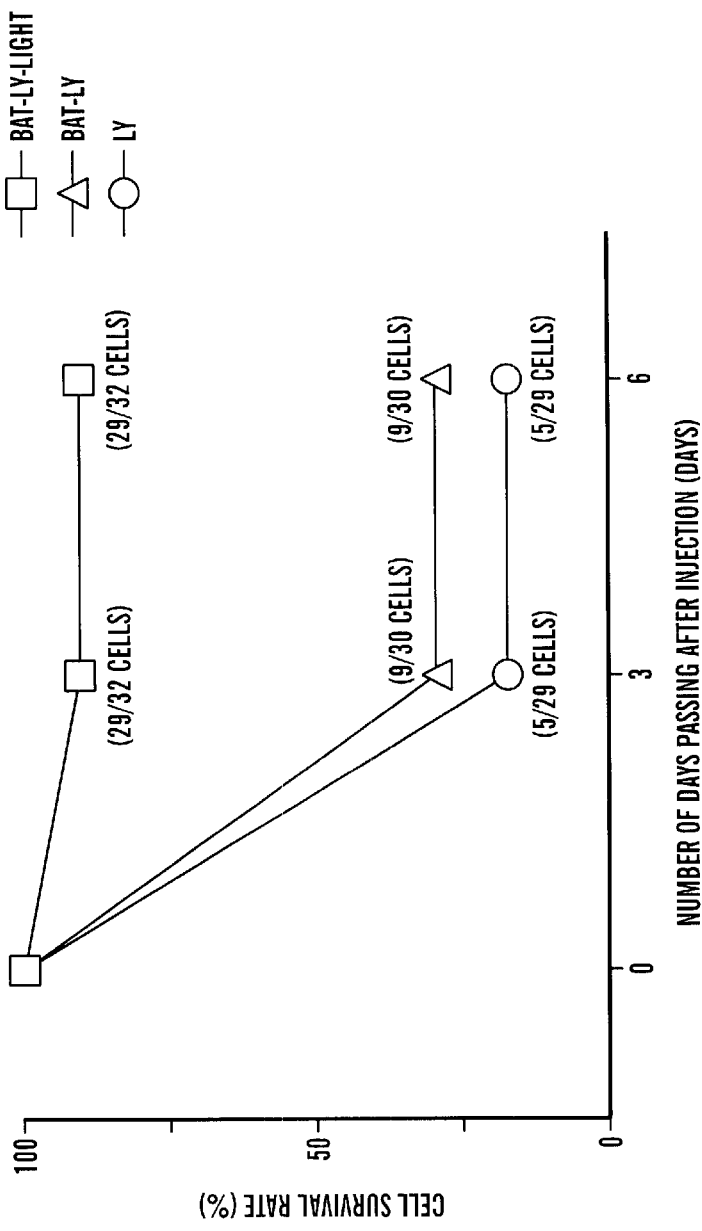
FIG. 12 shows a comparison of an injection success rate between a normal physical injection process and a new photosensitized injection process.

In FIG. 12, the axis of abscissa indicates injection process conditions, while the axis of ordinate indicates the injection success rate (unit: %).

With the BAT-containing injection liquid, an injection success rate of about 80% was achieved when ultraviolet light was applied for 2 minutes (the injection was attempted on 30 cells and was successful with 25 of them; 83%).

On the other hand, when no light was applied with the capillary kept in contact with the cell, dispersion of the LY into the cell was observed in almost no cases (n=30; the injection was successful with 4 cells; 13% In addition, with the injection liquid without the BAT, the injection success rate was between 0 and 10% at a capillary approach speed of 7 $\mu ms^{-1}$, whether or not UV light was applied (when UV light was applied, the injection was successful with none of the 30 cells; 0%) (when no UV light was applied, the injection was successful with 3 of the 30 cells; 10%).

A cell survival rate after the injection process was compared between cells subjected to the normal microinjection process using the physical shearing force and cells subjected to the photosensitizing microinjection.

The LY was injected into the cell by means of microinjection. In a dead cell with its cell membrane collapsed, the LY disperses quickly to lose its color [Cell, 14, 741–759 (1987)]. Thus, using a rate at which the cell subjected to the injection process holds the LY, as an index indicating the cell survival rate, the survival rates 3 and 6 days after the injection process were compared to each other. Results are shown in FIG. 13.

Figure 13:
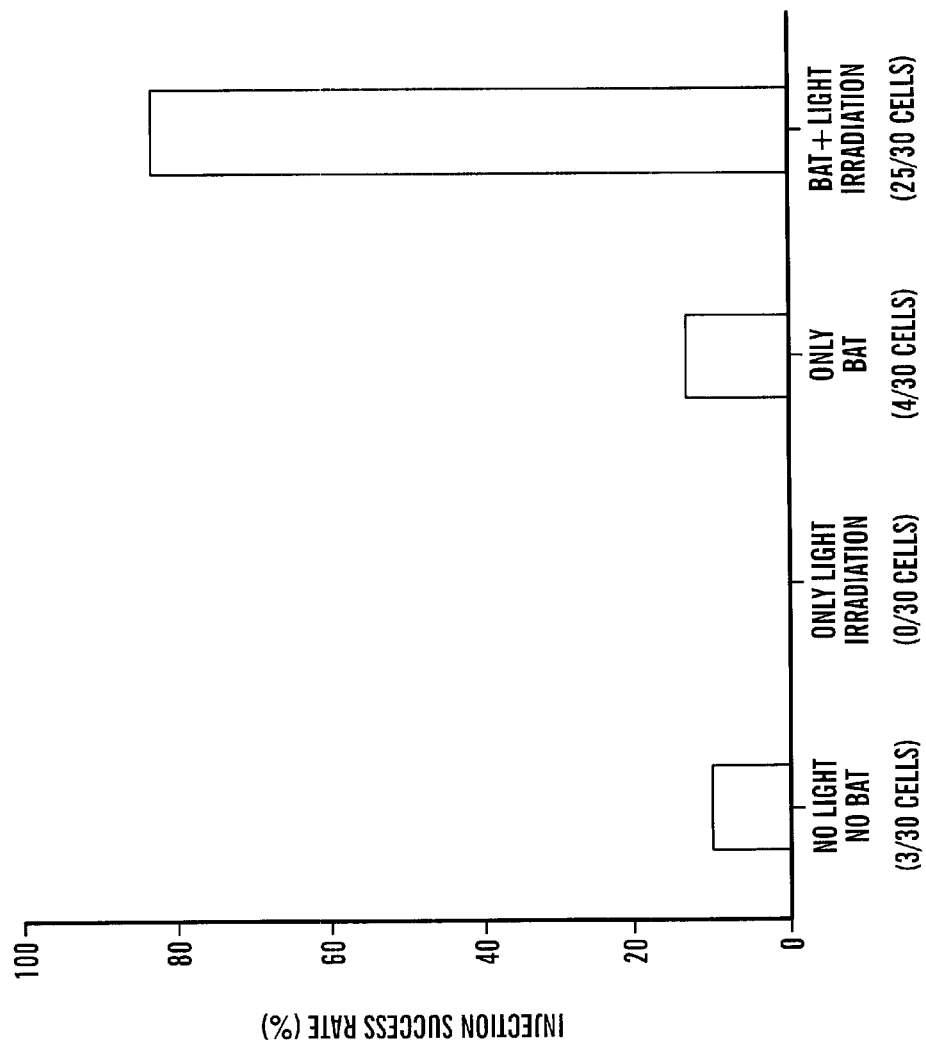
FIG. 13 shows a comparison of variations in cell survival rate after a cell injection process between the normal physical injection process and the new photosensitized injection process.
Figure 14A:
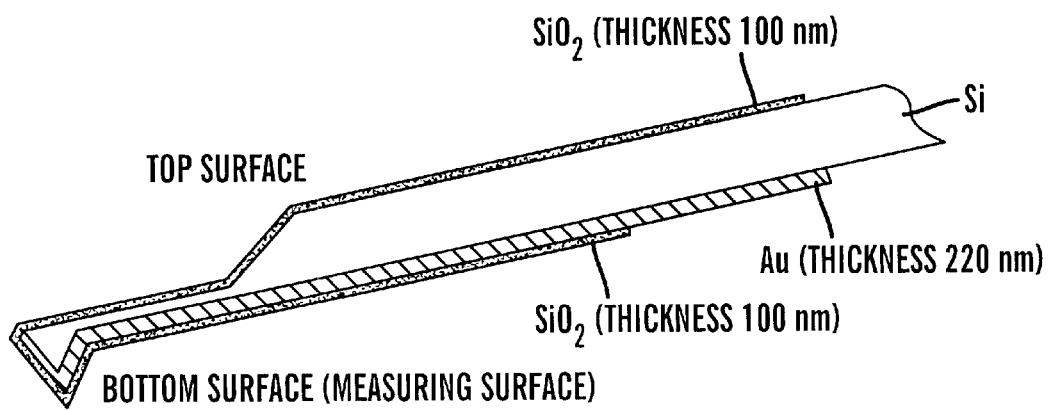
FIGS. 14A and 14B schematically show a minute electrode produced using a scanning probe of an atomic force microscope as a support.
Figure 14B:
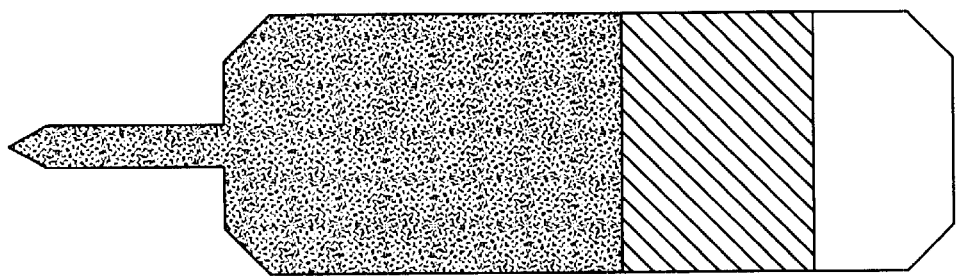

In FIG. 13, the axis of abscissa indicates the number of days passing after the injection process (unit: day), while the axis of ordinate indicates the survival rate (units %).

For the normal LY injection and the LY-BAT injection, which were control examples, the survival rate was observed to be 30% or lower 3 days after the injection (LY: 17%; BAT+LY: 30%). No change was observed between the LY retaining rate at day 3 and day 6 for all of the three injection Conditions.

For the present microinjection process, only 10% of the cells could be dyed with the LY when the injection liquid without the BAT was used or no light was applied to the cell. Contrary to these control processes, when the BAT-containing injection was used and light was applied to the cell, a rate at which the sell was successfully dyed with the LY was about 80%, which is significantly high. This indicates that the BAT contributed to punching the cell membrane when irradiated with light.

Alternatively, after the normal membrane-shearing injection, the cell survival rate was between 20 and 30% A cell survival rate of about 90% for the cells subjected to the photosensitizing injection indicates that this injection causes little damage to the cells.

The LY injected into the cell disperses quickly through the cytoplasm to dye the cells. However, in a dead cell with the ion barrier capability of the cell membrane lost, the LY disperses to the exterior of the cell 1 or 2 seconds after the injection. This quick dispersion of the LY has been reported to also occur through a gap junction, which is a liquid-liquid connecting path [Cell & Tissue Res., 234, 309–318 (1983)] [d. Neurosci., 14, 3945–3957 (1994)]. In view of this report on the quick dispersion of the LY, the punched cell membrane is assumed to be re-blocked in the cell holding the LY after the injection process. This prompt repair of the membrane is also supported by the fact that the membrane potential and resistance recover within several minutes after light irradiation in Example 3.

There are assumed to be two such membrane blocking mechanisms. one of them is a metabolic repair of an oxidized membrane effected by a cell oxidation-inhibiting mechanism [J. Neurochem., 68, 1904–1910 (1997)]. The other is a mechanism for blocking a damaged portion due to the fluidity of membrane lipid [Proc. Natl. Acad. Sci. 69, 2056–2060 (1972)] instead of biochemical repair of the membrane.

For the present injection process system, it is assumed that when the capillary is separated from the cell, cell membrane components on which the photosensitizer has had almost no effect start to flow to block the punched portion of the membrane. This assumption is based on the point that a similar prompt blockage of the cell membrane is observed in the case of a simple physical punching of the cell membrane. The physical punching of the cell membrane using a minute glass pipette or a patch pipette has been described above. After such physical punching, the punched portion of the cell membrane is often blocked after removal of the pipette, and such prompt re-blocking is assumed to result from the fluidity and self-organizing capability of the membrane lipid ["Living Membrane and Biological Energy [third edition], 7. Reorganization of Living Membrane", Tokyo University Publishing Association (1985)].

It is presumably at least impossible that membrane recovery based on biochemical metabolism allows the membrane to be re-blocked within a period in the order of several seconds. Of course the biochemical membrane repair occurs actually, but this mechanism is assumed to require a period of time in the order of several hours to several days to return the oxidized cell membrane to the normal state.

In view of the technique for connecting the electrode to the cell, it is very meaningful that the LY was injected into the cell by means of the photosensitizing injection. As described above, the Lx can permeate not only into a cell into which it has been injected but also into adjacent cells coupled thereto by means of the gap junction, so that all these cells are dyed [Cell & Tissue Res., 234, 309–318 (1983)][J. Neurosci., 14, 3945–3957 (1994)].

One of the functions of the gap junction is an electric connection between the cells [New Physiological System 7, Physiology for Generation and Differentiation, Chapter 4, Generation of Intercell Coupling, I. Electric Connection", Medical Publishing Company (1991)]. In response to an electric stimulus, myocardial cells or the like contract synchronously all over the muscle tissue because a large number of muscle cells are electrically connected together via the gap junction.

Since the present BAT photosensitizing injection enabled the cells to be dyed with the LY, an electric connection at least comparable to the gap junction is assumed to have been established between the liquid inside the capillary and the cytoplasm. That is, this result indicates that the electric connection was established by the light irradiation independently of the physical punching.

By adding the photosensitizer BAT to the injection liquid before the injection process, the possibility of the optically controlled punching technique independent of the physical shearing force has been demonstrated. Furthermore, the present photosensitizing injection is technically more advantageous than the normal microinjection based on the physical shearing force, in terms of damage to the cell caused by the injection.

EXAMPLE 6

Producing Membrane Destroying Member using Scanning Probe of Atomic Force Microscope A probe side (a measuring surface) of a commercially available monocrystal scanning probe processed by means of etching (manufactured by Nanosensors; single-beam silicon monocrystal scanning probe; cantilever length: about 130 $\mu$m) was plated with gold (Au) with a thickness of 220 nm by means of sputtering (Shibaura Production Company; sputter operation pressures 0.3 Pa; output: 100 W). Areas of the probe other than a measuring metal terminal and an equipment-connected metal terminal were insulated and covered by silicon dioxide of thickness 100 nm. This scanning probe was installed in an atomic force microscope (Nanoscope III; manufactured by Digital Instruments), and the equipment-side metal terminal was connected to a negative electrode of an electric punching apparatus (Gene Pulser; manufactured by BIO-RAD laboratories). A positive electrode of the electric punching apparatus was connected to a metal substrate (copper, platinum, or the like) on an AFM sample plate, and the probe, which had not had its insulation destroyed, that is, which was still insulated and coated by silicon dioxide, was brought in contact with the substrate. A 3-$\Omega$ resistor was connected in series between the scanning probe in contact with the substrate and the electric punching apparatus to prevent the probe from being destroyed by an excessive current after the insulation had been destroyed. A battery rating and voltage for the electric punching apparatus were set at 0.25 $\mu$F and 50 V, respectively, and electricity was instantaneously conducted between the substrate and the scanning probe section. This conduction caused the insulation at the tip portion of the probe to be destroyed to expose a metal layer from the tip portion. Thus, a minute Metal electrode was completed which had only the tip portion of the probe exposed as an electrode.

Further, the Lip portion of the probe of the minute metal electrode was immersed in an acid cater solution containing 2 mM of BAT (pH 3.0). This operation caused the BAT to be adsorbed by and fixed to the electrode. Finally, the electrode was washed off in distilled water to remove an excess portion of the BAT.

The above-described process was executed to produce a membrane destroying member, having the functions of the scanning probe of the atomic force microscope and the electrode functions.

INDUSTRIAL APPLICABILITY

The technique for controlling the membrane denaturation reaction without using the physical shearing force has been developed to enable the membrane to be denatured or punched more easily than before. The use of the minute metal electrode facilitates the insertion of the electrode into the cell using the minute metal electrode, as is difficult in the prior art, thereby enabling the membrane potential in the cell to be easily measured. The minute metal electrodes can be integrated together, so that a nerve interface far the barrier free technology can be developed.

What is claimed is:

1. An electrode comprising an insulated support, a conductive pattern formed on a surface of the insulated support, an insulator formed on the conductive pattern in such a manner that a portion on the conductive pattern which comes in contact with at least a cell membrane after the membrane has been penetrated, and a membrane denaturation reaction promoting portion formed in the portion coming in contact with the membrane or in a neighborhood thereof and having a membrane denaturing force other than a physical shearing force.

2. The electrode according to claim 1, wherein the insulated support comprises an insulating layer covering a surface of the support.

3. The electrode according to claim 1, wherein a compound that causes the membrane denaturation reaction promoting portion to induce a membrane denaturation reaction is applied or fixed to the electrode.

4. The electrode according to claim 3, wherein the membrane denaturation reaction utilizes a chained peroxidization reaction of membrane components started by a direct or indirect generation reaction of an activated oxygen species.

5. The electrode according to claim 3, wherein the membrane denaturation reaction includes a reaction induced by a particular stimulus and a reaction precursor to denature or destroy the membrane.

6. The electrode according to claim 5, wherein the particular , stimulus is light and the reaction precursor is a photosensitizing compound.

7. The electrode according to claim 1, wherein after the membrane has been denatured or destroyed, the electrode penetrates the membrane and the penetrated membrane comes in close contact only with part of the insulating portion.

8. The electrode according to claim 1, wherein the electrode is connected to a position controlling device, and a position where the electrode is inserted into or contacted with the membrane can be controlled.

9. The electrode according to claim 1, wherein the electrode is connected to a position controlling device and has a function for measuring a shape of a surface of the membrane or a solid.

10. The electrode according to claim 1, wherein the insulated support comprises a scanning probe of a scanning probe microscope.

11. The electrode according to claim 1, wherein at least a part of a measuring metal terminal is covered with an insulator membrane or a conductor membrane.

12. An interface type minute membrane potential measuring apparatus comprising the electrode according to claim 1 and a potential measuring device.

13. An electrode including a support comprising silicon processed by means of etching, wherein gold (Au) with a thickness of 220 nm is plated on a bottom surface (a measuring surface) of the support, areas of the electrode other than a measuring metal terminal and an equipment-connected metal terminal are insulated and covered by silicon dioxide with a thickness of 100 nm, and 5'5"-bis(aminomethyl)-2,2':5'2"-terthiophene is fixed to a portion of the electrode.

* * * * *